(12) United States Patent
Wu et al.

(10) Patent No.: US 8,017,622 B2
(45) Date of Patent: *Sep. 13, 2011

(54) OPIOID AND OPIOID-LIKE COMPOUNDS AND USES THEREOF

(75) Inventors: Edwin S. C. Wu, Cary, NC (US); Mao-Hsiung Yen, Taipei (TW)

(73) Assignee: Jenken Biosciences, Inc., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/400,344

(22) Filed: Mar. 9, 2009

(65) Prior Publication Data

US 2009/0169508 A1   Jul. 2, 2009

Related U.S. Application Data

(60) Division of application No. 11/104,281, filed on Apr. 12, 2005, now Pat. No. 7,501,433, which is a continuation-in-part of application No. 10/936,431, filed on Sep. 8, 2004, now Pat. No. 7,923,454, which is a continuation-in-part of application No. PCT/US03/15461, filed on May 16, 2003.

(60) Provisional application No. 60/518,448, filed on Nov. 7, 2003.

(51) Int. Cl.
*A61K 31/485* (2006.01)
*A61K 31/4748* (2006.01)

(52) U.S. Cl. .................. 514/282; 514/894; 514/893

(58) Field of Classification Search ................. 514/282, 514/894, 893; 546/45, 46
See application file for complete search history.

(56) References Cited

U.S. PATENT DOCUMENTS

| | | | |
|---|---|---|---|
| 3,275,638 A | 9/1966 | Sawa et al. |
| 3,764,606 A | 10/1973 | Akkerman et al. |
| 3,819,635 A | 6/1974 | Pachter et al. |
| 3,872,127 A | 3/1975 | Merz et al. |
| 3,923,987 A | 12/1975 | Merz et al. |
| 3,936,463 A | 2/1976 | Behner et al. |
| 4,029,798 A | 6/1977 | Yamamoto et al. |
| 4,128,548 A | 12/1978 | Akkerman et al. |
| 4,161,597 A | 7/1979 | Olofson et al. |
| 4,217,353 A | 8/1980 | Smith, Jr. |
| 4,228,285 A | 10/1980 | Montzka et al. |
| 4,230,712 A | 10/1980 | Kotick et al. |
| 4,267,182 A | 5/1981 | Holaday et al. |
| 4,272,541 A | 6/1981 | Kotick et al. |
| 4,288,444 A | 9/1981 | Akkerman et al. |
| 4,388,463 A | 6/1983 | Brossi et al. |
| 4,390,699 A | 6/1983 | Brossi et al. |
| 4,454,142 A | 6/1984 | Tuttle |
| 4,459,299 A | 7/1984 | Hosobuchi |
| 4,511,570 A | 4/1985 | Tuttle |
| 4,511,579 A | 4/1985 | Rotramel et al. |
| 4,600,718 A | 7/1986 | Huebner |
| 4,639,455 A | 1/1987 | Moore |
| 4,673,679 A | 6/1987 | Aungst et al. |
| 4,689,332 A | 8/1987 | McLaughlin et al. |
| 4,857,533 A | 8/1989 | Sherman et al. |
| 4,863,928 A | 9/1989 | Atkinson et al. |
| 4,873,076 A | 10/1989 | Fishman et al. |
| 4,877,791 A | 10/1989 | Sherman |
| 4,880,813 A | 11/1989 | Frost |
| 4,912,114 A | 3/1990 | Revesz |
| 4,923,875 A | 5/1990 | Frost |
| 4,946,848 A | 8/1990 | Tuttle et al. |
| 4,994,466 A | 2/1991 | Sherman et al. |
| 5,013,739 A | 5/1991 | Bihari et al. |
| 5,013,740 A | 5/1991 | Glover |
| 5,057,322 A | 10/1991 | Frost |
| 5,071,985 A | 12/1991 | Andre et al. |
| 5,086,058 A | 2/1992 | Sinclair et al. |
| 5,206,248 A | 4/1993 | Smith |
| 5,217,353 A | 6/1993 | De Filippis |
| 5,219,861 A | 6/1993 | Kanematsu et al. |
| 5,354,758 A | 10/1994 | Lawson et al. |
| 5,356,900 A | 10/1994 | Bihari et al. |
| 5,504,208 A | 4/1996 | Sobotik et al. |
| 5,607,941 A | 3/1997 | Merz et al. |
| 5,731,318 A | 3/1998 | Carter et al. |
| 5,780,479 A | 7/1998 | Kim |
| 5,817,665 A | 10/1998 | Dante |
| 5,856,332 A | 1/1999 | Dante |
| 5,878,750 A | 3/1999 | Clemens |
| 5,912,347 A | 6/1999 | Hudlicky et al. |
| 5,994,357 A | 11/1999 | Theoharides |
| 6,004,970 A | 12/1999 | O'Malley et al. |
| 6,150,524 A | 11/2000 | Hartmann et al. |
| 6,153,621 A | 11/2000 | Hamann |
| 6,166,211 A | 12/2000 | Cain et al. |

(Continued)

FOREIGN PATENT DOCUMENTS

CA   2072814   1/1993

(Continued)

OTHER PUBLICATIONS

Tyle, Praveen. "Iontophoretic Devices for Drug Delivery", *Pharmaceutical Research* (1986), 3(6): 318. Reich, I., et al. "Metrology and Calculations." in Remington, *The Sciences and Practice of Pharmacy* (PA, Mack Pub. Co. 9$^{th}$ Ed. (1995) ) Chap. 9, pp. 63-93; p. 82 (Calculating Dosages for Individuals).

Orlek, B.S. et al. "Comparison of Azabicyclic Esters and Oxadiazoles as Ligands for the Muscarinic Receptor", *J. Med. Chem.* (1991), 34(9): 2726-2735.

Wu, Chin-Chen et al. "Terbutaline Prevents Circulatory Failure and Mitigates Mortality in Rodents with Endotoxemia", *Shock* (2000), 14: 60-67.

Wu, Chin-Chen et al. "Evidence for Inducible Nitric Oxide Synthase in Spontaneously Hypertensive Rats", *Biochem. Biophys. Res. Commun.* (1996), 228: 459-466.

Chen, A. et al. "Glomerular Localization of Nephritogenic Protein Complexes on a Nonimmunologic Basis", *Lab. Invest.* (1992), 67: 175-185.

(Continued)

*Primary Examiner* — Charanjit Aulakh
(74) *Attorney, Agent, or Firm* — Ladas & Parry LLP

(57) ABSTRACT

The present invention relates to opioid and opioid-like compounds, and pharmaceutical formulations thereof, and use thereof for prevention and treatment of disorders such as septic shock and organ damage.

10 Claims, 6 Drawing Sheets

U.S. PATENT DOCUMENTS

| | | | |
|---|---|---|---|
| 6,242,604 | B1 | 6/2001 | Hudlicky et al. |
| 6,262,062 | B1 | 7/2001 | Clemens |
| 6,271,239 | B1 | 8/2001 | Portoghese |
| 6,288,074 | B1 | 9/2001 | Bihari |
| 6,316,411 | B1 | 11/2001 | Oeltgen et al. |
| 6,323,212 | B1 | 11/2001 | Nagase et al. |
| 6,384,044 | B1 | 5/2002 | Bihari |
| 6,525,062 | B2 | 2/2003 | Levine |
| 6,528,520 | B2 | 3/2003 | Clemens |
| 6,541,478 | B1 | 4/2003 | O'Malley et al. |
| 6,586,443 | B1 | 7/2003 | Bihari et al. |
| 6,645,938 | B2 | 11/2003 | Oeltgen et al. |
| 6,727,397 | B2 | 4/2004 | Basset et al. |
| 6,734,188 | B1 | 5/2004 | Rhodes et al. |
| 6,737,397 | B1 | 5/2004 | Zagon et al. |
| 6,737,400 | B2 | 5/2004 | Crain et al. |
| 7,501,433 | B2 * | 3/2009 | Wu et al. ............. 514/282 |
| 2001/0018413 | A1 | 8/2001 | Crain et al. |
| 2001/0046968 | A1 | 11/2001 | Zagon et al. |
| 2002/0045636 | A1 | 4/2002 | Clemens |
| 2002/0198227 | A1 | 12/2002 | Bernstein |
| 2003/0069262 | A1 | 4/2003 | Sadee et al. |
| 2003/0105121 | A1 | 6/2003 | Bihari |
| 2004/0122033 | A1 | 6/2004 | Nargund et al. |
| 2008/0015211 | A1 * | 1/2008 | Smith et al. ............ 514/286 |

FOREIGN PATENT DOCUMENTS

| | | |
|---|---|---|
| DE | 2 238 839 | 2/1974 |
| EP | 0 377 272 A2 | 9/1989 |
| EP | 367533 | 5/1990 |
| EP | 373744 | 6/1990 |
| EP | 0 377 272 | 7/1990 |
| EP | 0377272 | 7/1990 |
| EP | 0 402 899 A1 | 12/1990 |
| EP | 0242417 | 2/1993 |
| EP | 0577847 | 1/1994 |
| EP | 0 612 730 A1 | 8/1994 |
| EP | 0632041 | 1/1995 |
| EP | 0 663 401 | 7/1995 |
| EP | 471525 | 10/1995 |
| GB | 1038732 | 8/1966 |
| GB | 1077711 | 8/1967 |
| GB | 2175898 | 12/1986 |
| WO | 87/02586 | 5/1987 |
| WO | 98/05667 | 2/1998 |
| WO | 00/24395 | 5/2000 |
| WO | 00/56735 | 9/2000 |
| WO | 02/16367 | 2/2002 |
| WO | 02/36573 | 5/2002 |
| WO | 03/037340 | 5/2003 |

OTHER PUBLICATIONS

Olofson, R.A. et al. "A new reagent for the selective, high-yield N-dealkylation of tertiary amines: improved syntheses of naltrexone and nalbuphine", *J. Org. Chem.* (1984), 49(11): 2081-2082.

Lipsky, P.E. et al. "Infliximab and methotrexate in the treatment of rheumatoid arthritis", *N. Engl. J. Med.* (2000), 343:1594-1602.

Newton, R. C. and C. P. Decicco. "Therapeutic potential and strategies for inhibiting tumor necrosis factor-α.", *J. Med. Chem.* (1999), 42: 2295-2314.

Preiser et al. "Methylene blue administration in septic shock: a clinical trial", *Crit. Care Med.* (1995), 23: 259-264.

Gachot, B. et al. "Short term effects of methylene blue on hemodynamics and gas exchange in humans with septic shock", *Intensive Care Med.* (1995), 21: 1027-1031.

Vincent, J. L. et al. "Clinical trials of Immunomodulatory therapies in severe sepsis and septic shock", *CID* (2002), 34: 1084-1093.

Wolfe, John P. and Stephen L. Buchwald. "Improved Functional Group Compatibility in the Palladium Catalyzed Amination of Aryl Bromides", *Tetrahedron Letters* (1997), 38: 6359-6362.

Ahman, Jens and Stephen L. Buchwald. "An Improved Method for the Palladium-Catalyzed Amination of Aryl Triflates", *Tetrahedron Letters* (1997), 38: 6363-6366.

"Reactive Oxygen Species (ROS)", *R&D Systems—Mini-Review: Reactive Oxygen Species (ROS)*, copyright 2002. R&D Systems. www.rndsystems.com.

Channon, K. M. and T.J. Gutzik, "Mechanisms of superoxide production in human blood vessels: relationship to endothelial dysfunction, clinical and genetic risk factors", *J. Physiol Pharmacol.* (2002). 53(4): 515-524.

Henrotin, Y. E. et al. "The role of reactive oxygen species in homeostasis and degradation of cartilage", *OsteoArthritis and Cartilage* (2003), 11: 747-755.

Arzimanoglou, A. et al. "Epilepsy and neuroprotection: An illustrated review article", *Epileptic Discord.* (2000), 3: 173-182.

Seidman, M.D. et al. "Biologic activity of mitochondrial metabolites on aging and age-related hearing loss", *Am. J. Otol.* (2000), 21(2): 161-167.

McCord, J. M. and I. Fridovich. "Superoxide Dismutase: An Enzymic Function for Erythrocuprien (Hemocuprein)", *J. Biol. Chem.* (1969), 244: 6049-6055.

Feldmann, M. and R.N. Maini. "Discovery of TNF-α as a therapeutic target in rheumatoid arthritis: preclinical and clinical studies", *Joint Bone Spine* (2002), 69: 12-18.

Kim, Hyoung-Chun et al. "Anticonvulsant Effects of New Morphinan Derivatives", *Bioorg. Med. Chem Lett.* (2001), 11: 1651-1654.

Grauert, Matthias et al. "Synthesis and Structure-Activity Relationship of 6,7-Benzomorphan Derivatives as Antagonists of the NMDA Receptor-Channel Complex", *J. Med. Chem.* (1997), 40: 2922-2930.

Hamabe, Wakako et al. "(−)1-(Benzofuran-2-yl)-2-propylaminopentane Shows Survival Effect on Cortical Neurons Under Serum-free Condition Through Sigma Receptors", *Cell. Mol. Neurobiol.* (2000), 20(6): 695-702.

May, Everette L. et al. "Synthesis and in Vitro and in Vivo Activity of (−)-(1R,5R,9R)-and (+)· (1S,5S,9S)-N-Alkenyl-,-N-Alkynyl-, and -N-Cyanoalkyl-5,9-dimethyl-2'-hydroxy-6,7-benzomorphan Homologues", *J. Med. Chem.* (2000), 43(26): 5030-5036.

Chao, Chun C, et al. "Opiates, Glia, and Neurotoxicity", *Adv. Exp. Med. Biol.* (1996), 402: 29-33.

McGeer, Edith G. and Patrick L. McGeer. "The Role of the Immune System in Neurodegenerative Disorders", *Movement Disorders* (1997), 12: 855-858.

Liu, Bin et al. "Naloxone Protects Rat Dopaminergic Neurons against Inflammatory Damage through Inhibition of Microglia Activation and Superoxide Generation", *J. Pharmacol. Exp. Therap.* (2000), 293: 607-617.

Givens, J. R., et al., *Journal of Clinical Endocrinology. & Metabolism* 64/2, 1987, pp. 377-382 [abstract retrieved Sep. 27, 2005].

Schmidhammer, H. et al. "Synthesis and biological evaluation of 14-alkoxymorphinans. 1. Highly potent opioid agonists in the series of (−)-14-Methoxy-N-Methylmorphinan-6-ones" *J. Med. Chem.* (1984), 27(12): 1575-1579

Coop, A. et al. "Delta opioid binding selectivity of 3-Ether analogs of Naltrindole", *Bioorg. Med. Chem. Lett.* (1999), 9(24): 3435-3438.

Filer, C.N. et al. "Reduction of the N-Propargyl group with Tritium. General procedure for the preparation of N-'2,3-3H Allyl Opiate ligands at high specific activity", *J. Org. Chem.* (1981), 46: 4968-4970.

Jacobson, A. E. et al. "Paradoxical effects of N-cyanoalkyl substituents upon the activities of several classes of opioids", *J. Med. Chem.* (1979), 22(3): 328-331.

Koolpe, G.A. et al. "Diastereomeric 6-Desoxy-6-spiro-alpha-methylene-gamma-butyrolactone Derivative of Naltrexone and Oxymorphone . . .", *J. Med. Chem.* (1984). 27: 1718-1723.

"Morphinan", pp. 1073-1074. *The Merck Index: An Encyclopedia of Chemicals, Drugs and Biologicals*, 12th Edition Budavari, Susan et al., Editors. Whitehouse Station, NJ: Merck & Co., Inc. 1996.

Galinsky, R.E. et al. "Basic Pharmacokinetics." in Remington, *The Sciences and Practice of Pharmacy* (PA, Mack Pub. Co. 9th Ed. (1995) ) Chap. 42 pp. 724-740.

Rollins, D.E. "Clinical Pharmacokinetics." in Remington, *The Sciences and Practice of Pharmacy* (PA, Mack Pub. Co. 9th Ed. (1995) ) Chap. 43 pp. 741-751.

Li, Yuan, et al. "Morphine Enhances Hepatitis C Virus (HCV) Replicon Expression" *American Journal of Pathology* (2003) vol. 163, No. 3, pp. 1167-1175.

Lin, Shinn-Long, et al. "Effect of Naltrexone on Lipopolysaccharide-Induced Sepsis in Rats" *Journal of Biomedical Science* (2005) vol. 12, pp. 431-440.

Wang, Chien-Chuan, et al. "Dextromethorphan Prevents Circulatory Failure in Rats with Endotoxermia" *Journal of Medical Science* (2004) vol. 11, pp. 739-747.

Li, Guorong, et al. "Protective Effect of Dextromethorphan Against Endotoxic Shock in Mice" *Biochemical Pharmacology* (2005) vol. 69, pp. 233-240.

Jaume, Martial et al. "Opioid Receptor Blockade Reduces Fas-Induced Hepatitis in Mice" *Hepatology* (2004) vol. 40, No. 5, pp. 11I36-1143.

Zhang, Wei, et al. "Morphinan Neuroprotection: New Insight into the Therapy of Neurodegeneration." Critical Reviews™ in Neurobiology (2004) 16(4) pp. 271-302.

Brewer, C., et al. Naltrexone: report of lack of hepatotoxicity in acute viral hepatitis, with a review of the literature. Addiction Biology (2004) vol. 9, pp. 81-87.

Reents, S., et al. "Naloxone and Naltrexone application in COPD." Chest (1988) vol. 92, pp. 217-219.

Peer, G., et al. "Randomised crossover trial of naltrexone in uraemic pruritus." The Lancet (1996) vol. 348, pp. 1552-1554.

Bergasa, N., et al. "Oral nalmefene therapy reduces scratching activity due to the pruritus of cholestasis: A controlled study." J. Am. Acad. Dermatol. (1999) vol. 41. pp. 431-434.

Newman, A. H., "Synthesis and evaluation of 3-Substituted 17-Methylmorphinan Analogs as Potential Anticonvulsant Agents", J. MEd. Chem, 1992, 35, pp. 4135-4142.

Kigoshi, S., et al., "Effect of Several *d*-Morphinans on Ascites Tumors in Mice", Japn J. Pharmacol, 44, pp. 293-302, 1987.

Kim, H. C., et al., "Dextromethorphan modulates the AP-1 DNA-binding activity induced by kainic acid" Brain Research, 1999, pp. 125-132.

Kokubo, M., "Experimental studies on the antitumor activity of d-morphinan derivatives", Caplus, 1985, pp. 1-7.

Liu, Y., et al., "Dextromethorphan Protects Dopainergic Neurons against inflammation-Medicated Degeneration through Inhibition of Microglial Activation", J. Pharmacology and Experimental Therapeutics, vol. 35, No. 1, 2003, pp. 212-218.

Wang, H. H., et al., "Anti-amnesic effect of dimemorfan in mice", British Journal of Pharmacology, 2003, 138, pp. 941-949.

Peer, G., et al., "Randomised crossover trial of naltrexone in uraemic pruritus", Lancet, vol. 348, Dec. 7, 1996, pp. 1552-1554.

Reents, S.B., et al., "Naloxone and Naltrexone Application in OCPD", American College of Chest Physicians, 1988, pp. 217-219.

* cited by examiner

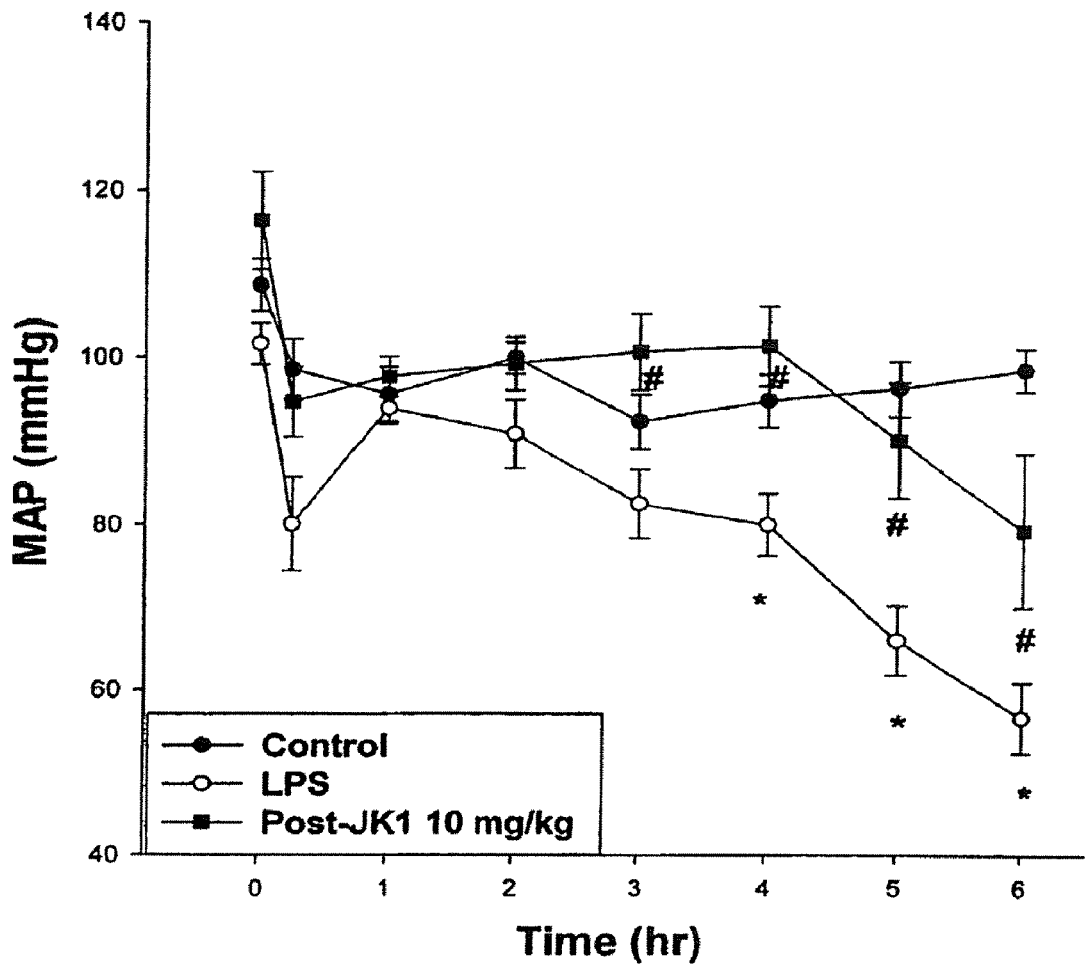
Figure 1. Effects of LPS-induced mean arterial blood pressure (MAP) changes. Post-treatment with XXV (10 mg/kg, i.v., n=8): 30 min after LPS (10 mg/kg, n=10). Data represent mean ± S.E.M., * p < 0.05 : LPS vs. Control (n=6) and # p < 0.05 : XXV vs. LPS.

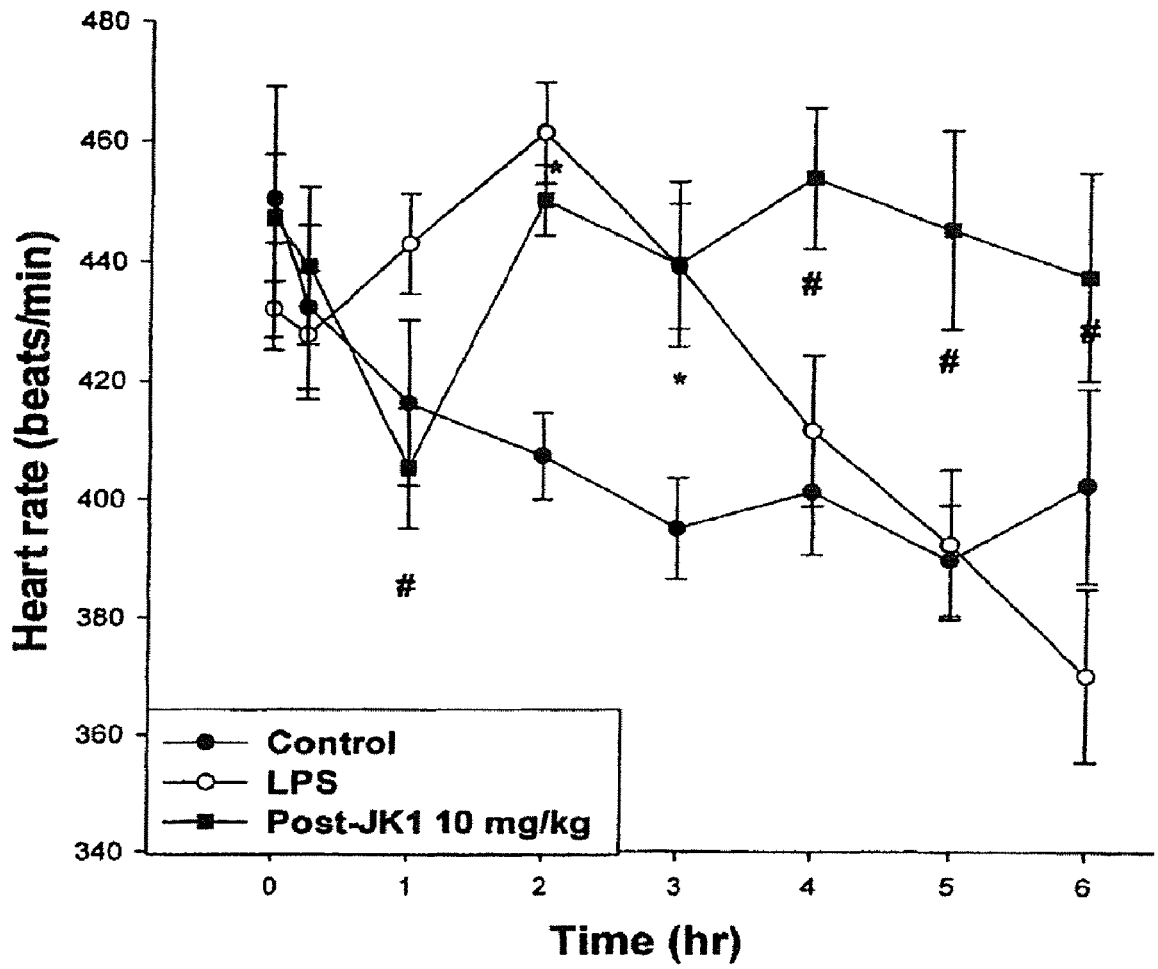
Figure 2. Effects of LPS-induced changes in heart rate (HR). Post-treatment with XXV (10 mg/kg, i.v., n=8) 30 min after LPS (10 mg/kg, n=10). Data represent mean ± S.E.M., * $p < 0.05$ : LPS vs. Control (n=6) and # $p < 0.05$ : XXV vs. LPS.

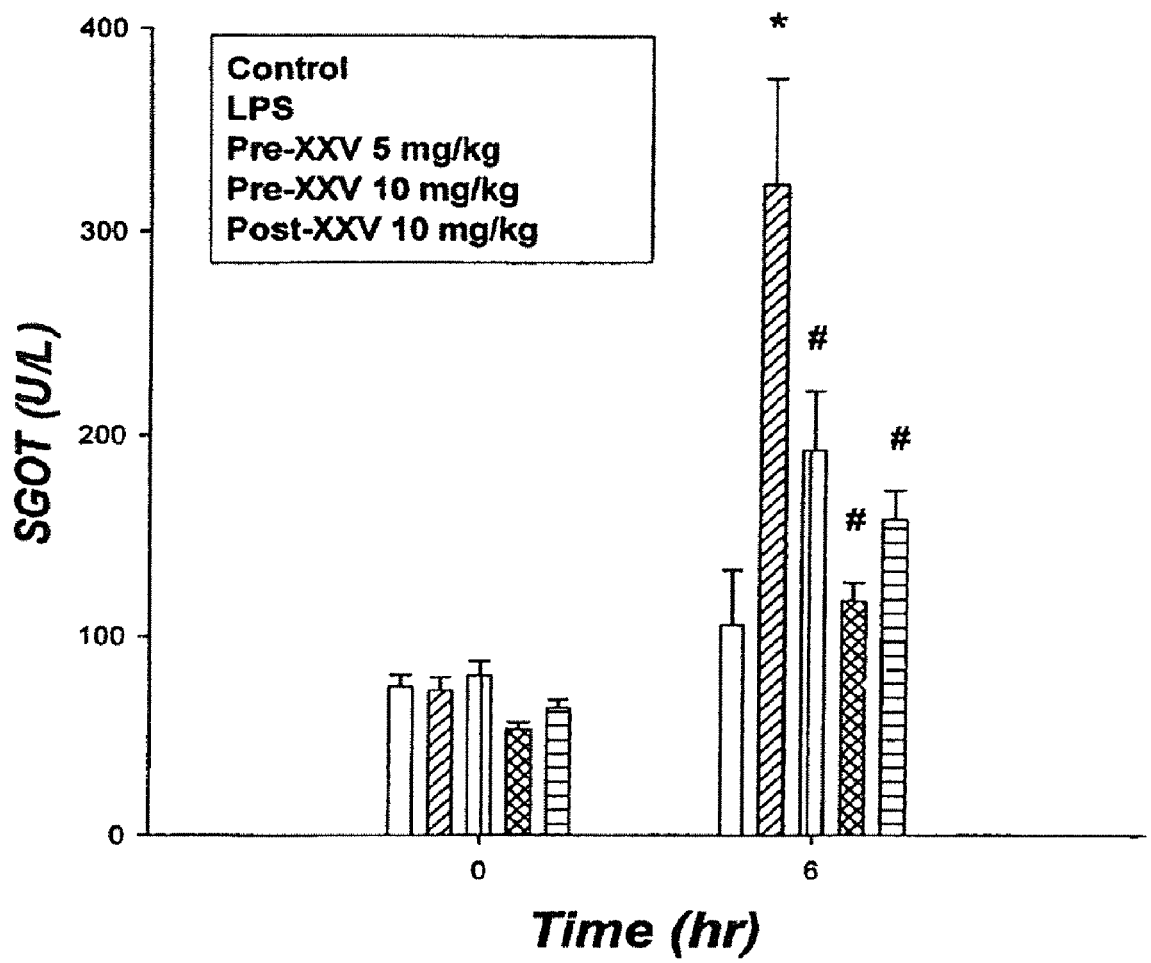
Figure 3. Effects of pre-treatment with XXV ( 5 mg/kg, i.v., n=9 and 10 mg/kg, i.v., n=10) and post-treatment XXV(10 mg/kg, i.v., n=6) on SGOT at 0 and 6 hr after LPS-treated rat (n=10). Data represent mean ± S.E.M., * $p < 0.05$ : LPS vs. Control (n=4) and # $p < 0.05$ : XXV vs. LPS

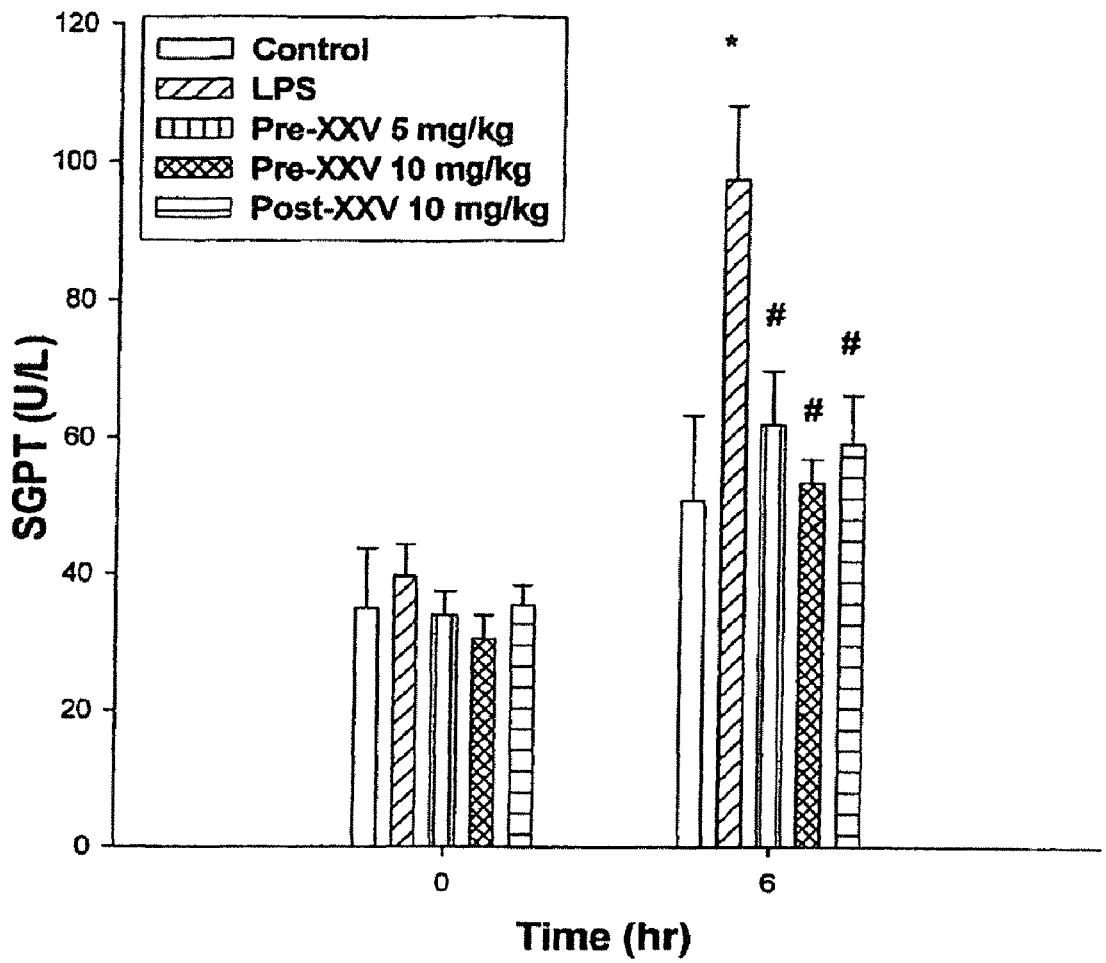
Figure 4. Effects of pre-treatment with XXV (5 mg/kg, i.v., n=9 and 10 mg/kg, i.v., n=10) and post-treatment XXV(10 mg/kg, i.v., n=6) on SGPT at 0 and 6 hr after LPS-treated rat (n=10). Data represent mean ± S.E.M., * $p < 0.05$ : LPS vs. Control (n=4) and # $p < 0.05$ : XXV vs. LPS.

Figure 5. Histopathological studies at high power (400x) of the light microscope showed morphologically relatively normal lung tissues from the group of rats receiving injections of XXVI alone [A] (n=2], marked thickness of PMN infiltration (arrow) in the group of the rats receiving injections of lipopolysaccharide (LPS) [B] (n=6), that was improved in the XXVI pretreatment group.

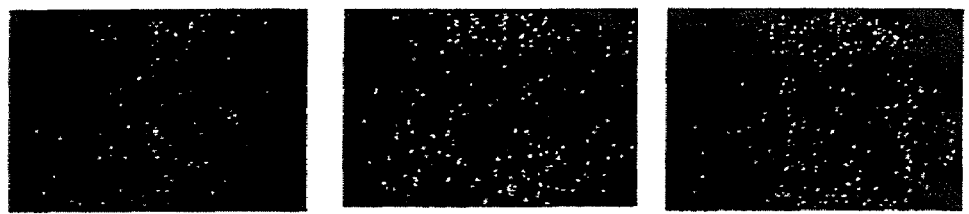

Figure 6. Histopathological studies at low power (40x) of the light microscope showed morphologically relatively normal lung tissues from the group of the rats receiving injections of XXVI alone [A] (n=2), marked thickness of alveolar wall with interstitial congestion and edema (arrow) in the group of the rats receiving injections of lipopolysaccharide (LPS) [B] (n=6), that was improved in the XXVI pretreatment group.

OPIOID AND OPIOID-LIKE COMPOUNDS AND USES THEREOF

CROSS REFERENCE TO RELATED APPLICATIONS

This is a divisional of application Ser. No. 11/104,281 filed on Apr. 12, 2005 now U.S. Pat. No. 7,501,433, which is a C-I-P of application Ser. No. 10/936,431 filed on Sep. 8, 2004 now U.S. Pat. No. 7,923,454 which claims benefit of Provisional Application No 60/518,448 filed on Nov. 7, 2003 and is a C-I-P of International Application PCT/US03/15461 filed on May 16, 2003, which designated the U.S., claims the benefit thereof and incorporates the same by reference.

FIELD OF THE INVENTION

The present invention relates to opioid and opioid-like compounds, and pharmaceutical formulations thereof, and use thereof for prevention and treatment of disorders such as septic shock and organ damage.

BACKGROUND OF THE INVENTION

Morphine is a known analgesic compound isolated from the opium poppy and has the following structural formula:

(I)

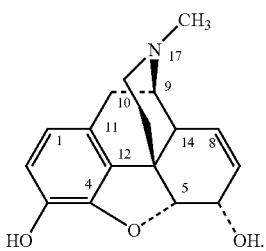

Although morphine is a potent analgesic, it possesses several undesirable side effects, including, but not limited to, physical dependence. Therefore, several compounds have been developed by addition or substitution to the basic morphine skeleton. Several such compounds are described in U.S. Pat. No. 5,219,347, issued Jun. 15, 1993 to Kanematsu, et al.; U.S. Pat. Nos. 5,912,347 and 6,242,604, issued Jun. 15, 1999 and Jun. 5, 2001 to Hudlicky et al.; U.S. Pat. No. 6,150,524, issued Nov. 21, 2000 to Hartmann et al.; U.S. Pat. No. 6,323,212, issued Nov. 27, 2001 to Nagese et al., and European Patent No. 577,847, published Jan. 12, 1994; European Patent No. 242,417, published Feb. 10, 1993; and European Patent No. 632,041, published Jan. 4, 1995. When a methoxy group is substituted for the 3-hydroxyl group, the compound is codeine, an opioid often used as an analgesic and also in cough medications for its antitussive effects.

Various substituents of the morphine structure are not required for a narcotic effect. Such morphine derivatives are classed as morphinans. As used in the present application, a morphinan is a compound similar to morphine but lacks the 4,5-ether, and may also lack the 7,8 alkenyl bond, and has the following structural formula:

(II)

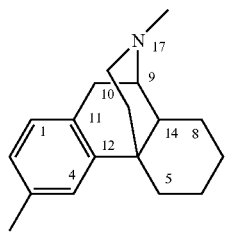

The numbering system used with compound (II) is a "conventional" numbering system used in describing morphinans and corresponds to the numbering of morphine (I) used above. It is recognized that the International Union of Pure and Applied Chemistry (IUPAC) numbering system is different, so that, e.g., the Merck Index (12 ed., 1996) names the compound Morphinan in monograph 6358 at pp. 1073-74 as [4aR(4aα,10α,10aα)]-1,3,4,9,10,10a-Hexahydro-2H-10,4a-iminoethano) phenanthrene and has the following structural formula:

(IIa)

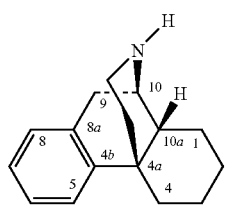

In the present application, the "conventional" numbering system is used unless otherwise noted.

Some morphinans are agonists, producing an analgesic effect while other morphinans are antagonists, blocking the effect of morphine and morphine agonists. Still other morphinans exhibit a combined agonist/antagonist activity, producing an analgesic effect itself while blocking the agonist activity of other morphinans. Finally, some morphinans, including the compound morphinan (IIa), exhibit no biological activity. The so-called "morphine rule," or Becket-Casey rule, requires (1) an aromatic ring (2) attached to a quaternary center which is connected to (3) a tertiary nitrogen which is (4) located two carbon atoms away. It has been found that substitution of the nitrogen methyl group by allyl, n-propyl, a substituted allyl, propynyl, cyclopropyl methyl, and cyclobutyl methyl results in morphine antagonists.

Representative morphinans are shown in the following patents: U.S. Pat. No. 3,275,638, issued Sep. 27, 1966 to Sawa et al.; U.S. Pat. No. 3,819,635, issued Jun. 25, 1974 to Pachter et al.; U.S. Pat. No. 4,228,285, issued Oct. 14, 1980; U.S. Pat. No. 4,673,679, issued Jun. 16, 1987 to Aungst et al.; U.S. Pat. No. 4,912,114, issued Mar. 27, 1990 to L. Revesz and U.K. Patent No. 2,175,898, published Dec. 10, 1986; U.S. Pat. No. 5,071,985, issued Dec. 10, 1991 to Andre et al.; U.S. Pat. No. 5,504,208, issued Apr. 2, 1996 to Sobotik et al.; U.S. Pat. No. 6,166,211, issued Dec. 26, 2000 to Cain et al.; and U.K. Patent No. 1,038,732, published Aug. 2, 1967.

A further simplification of the morphine structure involves elimination of one of the cycloalkane rings to produce 6,7 benzomorphans having the structural formula:

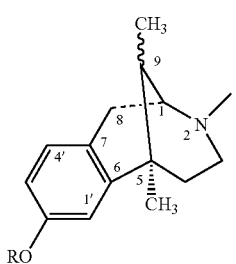

(III)

Representative benzomorphans are shown in the following patents: U.S. Pat. No. 3,764,606, issued Oct. 9, 1973 to Akkerman et al.; U.S. Pat. No. 3,936,463, issued Feb. 3, 1976 to Behner et al.; U.S. Pat. No. 4,029,798, issued Jun. 14, 1977 to Yamamoto et al.; U.S. Pat. No. 4,128,548, issued Dec. 5, 1978 to Akkerman et al.; U.S. Pat. No. 4,288,444, issued Sep. 8, 1981 to Akkerman et al.; U.S. Pat. No. 5,354,758, issued Oct. 11, 1994 to Lawson et al.; U.S. Pat. No. 5,607,941, issued Mar. 4, 1997 to Merz et al., U.S. Pat. No. 5,731,318, issued Mar. 24, 1998 to Carter et al., and Canadian Patent No. 2,072,814, published Jan. 3, 1993; U.K. Patent No. 1,077,711, published Aug. 2, 1967.

Another class of morphine derivatives, the morphones, feature an oxidized oxygen atom at C6, and have the following structural formula:

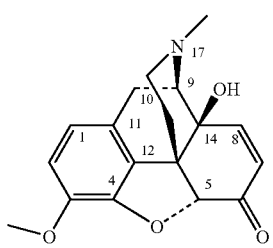

(IV)

Representative morphone compounds are described in the following patents: U.S. Pat. No. 4,230,712, issued Oct. 28, 1980 to Kotick et al.; U.S. Pat. No. 4,272,541, issued Jun. 9, 1981, also to Kotick et al.; U.S. Pat. No. 4,388,463, issued Jun. 14, 1983 to Brossi et al.; U.S. Pat. No. 4,390,699, issued Jun. 28, 1983, also to Brossi et al.; U.S. Pat. No. 5,780,479, issued Jul. 14, 1998 to S. W. Kim; and U.S. Pat. No. 6,271,239, issued Aug. 7, 2001 to Portoghese et al.

EP 377272 (Baker Cummin Pharma) discloses nalmefene and naltrexone for treatment in arthritic and inflammatory diseases.

U.S. Pat. No. 4,267,182 (Holaday et al) discloses the use of naloxone, natltrexone, nalorphine, diprenorphine, lavallorphan, pentazocine, metazocine, cyclazocine and etazocine for treatment of shock.

WO 98/05667 (Johnson Matthey) describes the production of hydrocodone and hydromorphone.

WO 02/16367 (Glaxo Wellcome Australia) describes N-demethylating N-morphinanes to produce intermadiates that can be used to replace the methyl group with groups such as allyl and cyclopropylmethyl groups.

WO 02/36573 ((Rensselaer Polytrchnic) describes varipous benzazocines which are useful as analgesics, anyi-diarrheal agents, anticonvulsants, antitussives and anti-addiction agents.

WO 00/56735 (Endo Pharmaceuticals) describes the production of 10-keto derivatives from morphians such as naloxone.

J. Org Chem vol 49 (June 1984) pages 2081-2 describes an imporved synthesis of naltrexone and nalbuphine"

Schmidhammer et al J. Med. Chem. 27 (No 12) 1575-1579 (1984) describes oxymorphone and its 3-benzyloxy analog.

Coop et al. Bioorganic & Medicianl Chemistry Letters vol 9 pages 3435-8 (1999) compounds similar to those of structure V of the present invention but wherein wherein X is cyclopropylmethyl and R is hydrogen, bezyl, phenylethyl or phenylpropyl.

German 2238839 (Boehringer, Sohn and Ingelheim) describes the production of compounds similar to those of formula VII of the present invention wherein R as set out in formula VII is hydrogen, methyl or acetyl and our X as furyl methyl or thienyl methyl.

U.S. Pat. No. 4,161,597 (Olofson) describes reactions of 14-hydroxymorphinans.

WO 03/037340 (Pain Therapeutics). describes the use of opioid inhibitors in increasing efficiency of certain anti-tumor agents. Compounds of structure V of the present invention where R is hydrogen and groups in the position corresponding to X are cycloalkylalkyl, allyl, or arylalkyl are included.

EP 663401 (Toray) describes an extremely large number of morphinan derivatives for use as analgesics, diuretics, antitussives and brain cell protective agents.

Filer et al J. Org. Chem. Vol 46 pages 4968-70 describes compounds similar to those of formula V of the present invention wherein R is hydrogen and our X is allyl or methyl ethynyl.

Jacobson et al J. Med. Chem. Vol 22 No. 3 pages 328-331 (1979) describes compounds similar to those of structure V of the present invention with R as hydrogen and X is hydrogen or ethylene nitrile.

Koolpe et al J. Med. Chem. Vol 27 pages 1718-23 (1984) discusses naltrexone and oxymorphone binding mechanisms.

Previous work in this area has generally focused upon the investigation of the use of these morphine derivatives as analgesics, morphine antagonists, or antitussives. However, recent literature has reported potential new uses for some morphine derivatives which may not be mediated through morphine receptors. A series of compounds that are modified in position 3 and 17 of the morphinan ring system have been reported to exhibit anticonvulsant effects in *Bioorg. Med. Chem. Lett.* 11, 1651-1654 (2001). A series of stereoisomeric 6,7-benzomorphan derivatives with modified N-substituents are described in *J. Med. Chem.* 40, 2922-2930 (1997) as antagonizing the N-methyl-D-aspartate (NNMA) receptor-channel complex in vitro and in vivo. (+)-Pentazocine, a sigma receptor agonist, has been demonstrated to have unique survival activity on cortical neurons through sigma receptors in *Cell. Mol. Neurobiol.* 20(6), 695-702 (2000). Two homologs in the (+)-(1S,5S,9S) -normetazocine series, N-pent-4-enyl and N-hex-5-enyl, are reported in *J. Med. Chem.* 43(26), 5030-5036 (2000), to have high-affinity and selective σ1-ligands (Ki=2 nM, σ2/σ1=1250, and 1 nM, σ2/σ1=750, resp.); in contrast, N-allylnormetazocine has relatively poor affinity at σ1, and its σ1/σ2 ratio is <100.

Recent advances in the research of neurodegenerative diseases of the central nervous system have revealed that the opioids may play a role in modulating the expression of inflammatory factors such as proinflammatory cytokines, free radicals and metabolites of arachidonic acid in microglia and in the mediation of immune-related neurodegeneration, *Adv. Exp. Med. Biol.* 402: 29-33 (1996); *Mov. Disord.* 12: 855-858 (1997). Naloxone, a morphine antagonist, is disclosed in *J. Pharmacol. Exp. Therap.* 293, 607-617 (2000) to protect rat dopaminergic neurons against inflammatory damage through inhibition of microglia activation and superoxide generation.

The potential for the development of tolerance and physical dependence with repeated opioid use is a characteristic feature of all the opioid drugs, and the possibility of developing psychological dependence (i.e., addiction) is one of the major concerns in the use of the treatment of pain with opioids. Another major concern associated with the use of opioids is the diversion of these drugs from the patient in pain to another (non-patient) for recreational purposes, e.g., to an addict. Thus, it is desirable to provide opioid and opioid-like compounds useful for the prevention or treatment of various disorders as described herein.

Aerobic organisms, which derive their energy from the reduction of oxygen, are susceptible to the damaging actions of the small amounts of $O_2-$, OH and $H_2O_2$ that inevitably form during the metabolism of oxygen, especially in the reduction of oxygen by the electron transfer system of mitochondria. These three species, together with unstable intermediates in the peroxidation of lipids, are referred to as Reactive Oxygen Species (ROS). Many diseases such as, but not limited to, Alzheimer's Disease, Parkinson's disease, aging, cancer, myocardial infarction, atherosclerosis, autoimmune diseases, radiation injury, emphysema, sunburn, and joint disease (a. *Everything cytokine & beyond*, Cytokines Mini-Reviews, Chapter:Reactive Oxygen Species (ROS), Copyright 2003 ©R&D Systems; b. Channon K M, Guzik T J, Mechanisms of superoxide production in human blood vessels: relationship to endothelial dysfunction, clinical and genetic risk factors. *J. Physiol. Pharmacol.* 2002, 53(4), 515-524; c. Henrotin, Y E et al. The role of reactive oxygen species in homeostasis and degradation of cartilage. *OsteoArthritis and Cartilage* 2003, 11, 747-755; d. Arzimanoglou A et al. Epilepsy and neuroprotection: An illustrated review article. *Epileptic Disord* 2002, 3, 173-82; e. Seidman M D et al., Biologic activity of mitochondrial metabolites on aging and age-related hearing loss.

*Am J Otol* 2000, 21(2):161-7.) are linked to damage from ROS as a result of an imbalance between radical-generating and radical-scavenging systems—a condition called oxidative stress. The discovery by McCord and Fridovich (McCord, J. M. & I. Fridovich *J. Biol. Chem.* 1969, 244:6049) of the superoxide dismutase (SOD) activity of erythrocuprein, together with the finding that almost all mammalian cells contain SOD, suggests a physiological role of at least the central ROS, superoxide.

TNF-α (tissue necrosis factor), a cytokine that plays a critical role in eliciting the body's inflammatory response and is present in abnormally high levels in the joints of individuals suffering from rheumatoid arthritis, has been implicated as an immune modulator in the immune system. Inhibitors of TNF-α have been shown to halt the progression of cartilage destruction and relieve the symptoms of severe arthritis. Approximately 30% of moderate to severe arthritic patients are not responsive to these treatments (Feldman M, Maini R N, Discovery of TNF-α as a therapeutic target in rheumatoid arthritis: preclinical and clinical studies. *Joint Bone Spine* 2002, 69, 12-18; Lipsky P E, et al. Infliximab and methotrexate in the treatment of rheumatoid arthritis. *N. Engl. J. Med.* 2000, 343 1954-1602). Animal studies in association with studies conducted in humans indicate a potential role for TNF modulation in Crohn's disease. ulcerative colitis, insulin resistance, multiple sclerosis, multiple organ failure, pulmonary fibrosis, and atherosclerosis (Newton R C, Decicco C P, Therapeutic potential and strategies for inhibiting tumor necrosis factor-a. *J. Med. Chem.* 1999, 42, 2295-2314). Biswas P, et al. reported that TNF-α drives HIV-1 replication in U937 cell clones (Biswas P, et al. Tumor necrosis factor-alpha drives HIV-1 replication in U937 cell clones and upregulates CXCR4. *Cytokine.* 2001,13, 55-59). Liver damages are associated with TNF-α release have been reported recently (McClain C J, et al. Advances in Alcoholic Liver Disease, *Current Gastroenterology Reports*, 2004, 6, 71-76).

During the course of sepsis, nitric oxide (NO) is produced. Its metabolites impair normal vascular reactivity, in conjunction with elevated endotoxin levels. Inhibitors of NO synthase restore blood pressure, lower the cardiac index and increase pulmonary and systemic vascular resistance. Selective NOS inhibitors targeted against iNOS may prove to be beneficial. A small study with an inhibitor of NOS action, namely methylene blue, which inhibits the associated guanylyl cyclase enzyme, has indicated beneficial effects versus the cardiovascular parameters described above in patients with septic shock [Preiser, J C, Lejeune P, Roman A, et al. Methylene blue administration in septic shock: a clinical trial. Crit. Care Med., 23: 259-64 (1995); Gachot B, Bedos J P, Veber B, et al. Short term effects of methylene blue on hemodynamics and gas exchange in humans with septic shock, Intensive Care Med 21:1027-31; Vincent, J L, Sun Q, Dubois, M-J, Clinical Trials of Immunomodulatory Therapies in Severe Sepsis and Septic Shock, CID, 34: 1084-1093 (2002)].

SUMMARY OF THE INVENTION

According to embodiments of the present invention, the present invention relates to a compound according to the formula R-A-X wherein:

R can be H, alkyl, allyl, phenyl, benzyl, or $(CH_2)_mR_4$, wherein m is from 0 to 6, and $R_4$ can be a ring structure. Such ring structures can be, for example, phenyl, naphthyl, and biphenyl, wherein the ring is optionally substituted with one to three substituents selected from the group consisting of halogen, alkyl, $NO_2$, CN, $CF_3$, and lower alkoxy $R_4$ can be a five-membered heterocyclic ring having one or more heteroatoms selected from the group consisting of O, S, and N, wherein the heterocyclic ring is substituted with a lower alkyl or a substituted phenyl group; $R_4$ can be a pyridine ring wherein the pyridine ring is optionally substituted with halogen, alkyl, $NO_2$, CN, $CF_3$, $OCH_3$, or $NR_1R_2$, where $R_1$ and $R_2$ are each independently H or alkyl, or $R_1$ and $R_2$ together with the nitrogen to which they are bound jointly form a cyclic ring, wherein the cyclic ring is a 3- to 7-membered alicyclic ring optionally having a double bond in the ring. $R_4$ can be quinoline. $R_4$ can be isoquinoline. $R_4$ can be 4-cyclohexylphenyl. $R_4$ can be a cyclic ring, wherein the cyclic ring is a 3- to 7-membered alicyclic ring optionally having a double bond in the ring;

A can be a structure such as one of the following structures:

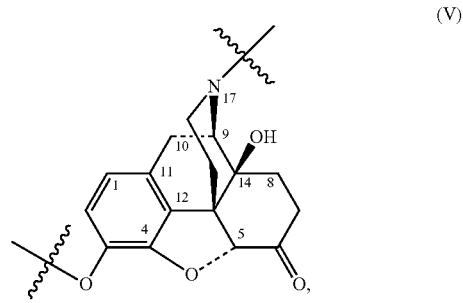

(V)

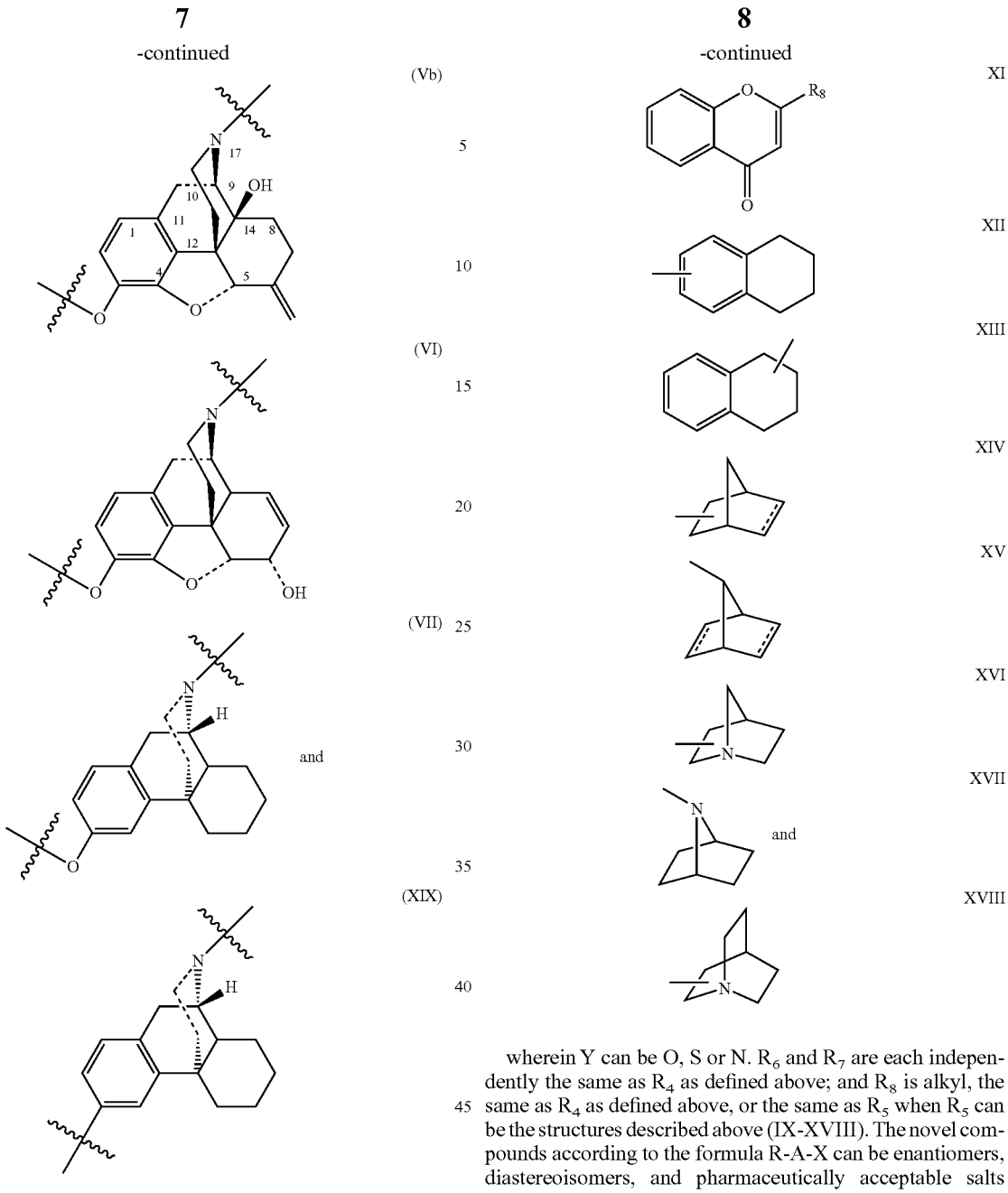

X can be hydrogen, allyl, cinnamoyl, crotonyl, $(CH_2)C_6H_5$-4F, $(CH_2)_nC\!=\!CR_1R_2$, $(CH_2)_nC\!\equiv\!CR_3$, $(CH_2)_nR_5$, and $(CH_2)_mCHR_6R_7$, wherein m is 0 to 6 and n is from 0 to 6. $R_3$ can be H, alkyl, or the same as $R_4$, wherein $R_4$ is described above and $R_5$ can be alkyl, CN, $COR_8$, or structures selected from the group consisting of the following structures:

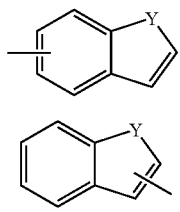

wherein Y can be O, S or N. $R_6$ and $R_7$ are each independently the same as $R_4$ as defined above; and $R_8$ is alkyl, the same as $R_4$ as defined above, or the same as $R_5$ when $R_5$ can be the structures described above (IX-XVIII). The novel compounds according to the formula R-A-X can be enantiomers, diastereoisomers, and pharmaceutically acceptable salts thereof. According to some embodiments, when A is the structure according to formulas V, VI and VII, and R is H, alkyl, allyl, or benzyl, X is not $(CH_2)_nC\!=\!CR_1R_2$, $(CH_2)_nC\!\equiv\!CR_3$, $(CH_2)_nR_5$, wherein n is from 0 to 6, $R_1$ and $R_2$ are described as above, $R_3$ is H, alkyl, or the same as $R_4$, wherein $R_4$ is phenyl, and $R_5$ is alkyl, CN and $COR_8$, wherein $R_8$ is alkyl or the same as $R_4$, wherein $R_4$ is a five-membered heterocyclic ring having one or more heteroatoms selected from the group consisting of O, S, and N.

Some compounds covered by the above formulae are known and we make no claim to them. In particular we make no claim to compounds i) where A is of structure V and Vb and
(a) R is hydrogen and X is allyl;
(b) R is methyl and X is methyl;
(c) R as hydrogen and X as methyl;
(d) R is hydrogen, methyl or ethyl and X is methyl;
(e) R as hydrogen or benzyl and X as methyl;
(f) R is hydrogen, methyl or acetyl and X is hydrogen;

(g) R is hydrogen and our X is allyl or methyl ethynyl;
(h) R is hydrogen and X is hydrogen or ethylene nitrile; group;
(i) R is hydrogen, methyl and X is phenyl;
ii) where A is formula VI and
(a) R is hydrogen, methyl or ethyl and X as methyl;
(b) R as hydrogen and X of our definition is allyl;
(c) R is hydrogen of $C_{1-4}$ alkyl and X is $C_{1-4}$ alkyl or alkenyl, $C_{3-4}$ cycloalkyl, $C_{3-4}$ cycloalkyl alkyl or $C_{3-4}$ cycloalkyl carbonyl;
(d) R is hydrogen of $C_{1-4}$ alkyl and X is $C_{1-4}$ alkyl or alkenyl, $C_{3-4}$ cycloalkyl;
iii) where A is formula VII and
(a) R as hydrogen and X as allyl;
(b) R is hydrogen of $C_{1-4}$ alkyl and X is $C_{1-4}$ alkyl or alkenyl, $C_{3-4}$ cycloalkyl, $C_{3-4}$ cycloalkyl alkyl or $C_{3-4}$ cycloalkyl carbonyl; and
iv) where A is formula XIX and
R is hydrogen, C1-C3 alkyl, a five-membered heterocyclic group and X as methyl, other alkyl, alkenylmethylene, arylmethyl, heterocyclylmethyl, or benzyl.

According to other embodiments of the present invention, the invention relates to methods of preventing or treating viral infections and conditions such as septic shock, inflammation, organ damage, neurological disorders, neurodegenerative diseases, cancer, cardiac disorders, and diseases associated with overproduction of superoxide anion radical, TNF-α, or iNOS, comprising administering to a subject in need thereof, a pharmaceutical composition comprising a therapeutically effective amount of a compound of formula R-A-X described above.

According to still other embodiments, the present invention relates to methods of preventing or treating viral infections and conditions selected from the group consisting of septic shock, inflammation, organ damage, neurological disorders, neurodegenerative diseases, cancer, and cardiac disorders, and diseases associated with overproduction or superoxide anion radical, TNF-α, or iNOS, comprising administering to a subject in need thereof, a pharmaceutical composition comprising a therapeutically effective amount of compound according to the formula R-A-X wherein:
R is methyl;
A has the following structure:

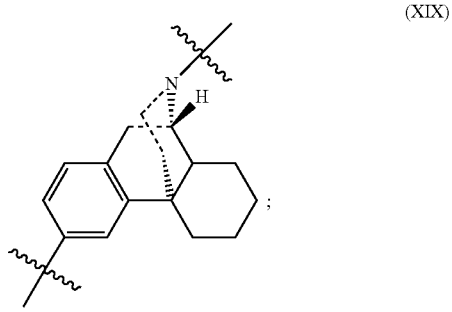

(XIX)

and
X can be hydrogen, methyl, cyclobutyl $(CH_2)_4$, n-propyl, CN, allyl, $CH_2=C(CH_2)_2$, or enantiomers, diastereoisomers, and pharmaceutically acceptable salts thereof.

According to yet other embodiments of the present invention, the present invention relates to methods of preventing or treating viral infections and conditions such as septic shock, organ damage, neurological disorders, neurodegenerative diseases, cancer, and cardiac disorders, and diseases associated with overproduction or superoxide anion radical, TNF-α, or iNOS, comprising administering to a subject in need thereof, a pharmaceutical composition comprising a therapeutically effective amount of opioid and opioid-like compounds, and derivatives and analogs thereof.

BRIEF DESCRIPTION OF DRAWINGS

FIG. 1 illustrates effects of XXV post-treatment on mean arterial blood pressure (MAP) in rats treated with lipopolysaccharide (LPS).

FIG. 2 illustrates effects of XXV post-treatment on heart rate in rats treated with lipopolysaccharide (LPS).

FIG. 3 illustrates effects of XXV treatment on plasma levels of serum glutamate-oxalate-transferase (SGOT) in rats treated with lipopolysaccharide (LPS).

FIG. 4 illustrates effects of XXV treatment on plasma levels of serum glutamic pyrate transaminase (SGPT) in rats treated with lipopolysaccharide (LPS).

FIG. 5 illustrates PMN filtration through histological studies of normal lung tissues of rats receiving (A) XXVI alone, (B) injections of lipopolysaccharide (LPS), and (C) pretreatment with XXVI.

FIG. 6 illustrates effects on the alveolar wall through histological studies of normal lung tissues of rats receiving (A) XXVI alone, (B) injections of lipopolysaccharide (LPS), and (C) pretreatment with XXVI.

DETAILED DESCRIPTION OF PREFERRED EMBODIMENTS

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, patent applications, patents and other references cited herein are incorporated by reference in their entireties for the teachings relevant to the sentence and/or paragraph in which the reference is presented.

The term "alkyl" as used herein refers to C1-C20 inclusive, linear, branched, or cyclic, saturated or unsaturated hydrocarbon chains, including for example, methyl, ethyl, propyl, isopropyl, butyl, isobutyl, tert-butyl, pentyl, hexyl, octyl, ethenyl, propenyl, butenyl, pentyl, hexenyl, octenyl, butadienyl, and allenyl groups. Alkyl groups can either be unsubstituted or substituted with one or more non-interfering substituents, e.g., halogen, alkoxy, acyloxy, hydroxy, mercapto, carboxy, benzyloxy, phenyl, benzyl, or other functionality which has been suitably blocked with a protecting group so as to render the functionality non-interfering. Each substituent may be optionally substituted with additional non-interfering substituents. The term "non-interfering" characterizes the substituents as not adversely affecting any reactions to be performed in accordance with the process of this invention.

The term "lower alkyl" as used herein refers to C1 to C8 alkyl, including C1 to C3, C1 to C4, C1 to C5, C1 to C6, and C1 to C7, which may be linear or branched and saturated or unsaturated.

The term "cycloalkyl" as used herein is typically C3, C4 or C5 to C6 or C8 cycloalkyl.

The term "aryl" as used herein refers to C6 to C10 cyclic aromatic groups such as phenyl, benzyl, naphthyl, and the like, and includes substituted aryl groups such as tolyl.

The term "heterocycle" as used herein refers to a monovalent saturated, unsaturated, or aromatic carbocyclic group having a single ring or multiple condensed ring and having at least one hetero atom, such as N, O, or S, within the ring, which can optionally be unsubstituted or substituted with hydroxy, alkyl, alkoxy, halo, mercapto, and other non-interfering substituents. Examples of nitrogen heterocycles include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline.

The term "halo" as used herein refers to any halogen group, such as chloro, fluoro, bromo, or iodo.

The term "opioid" as used herein refers to compounds that exhibit opium or morphine-like properties, including agonist and antagonist activity wherein such compounds can interact with stereospecific and saturable binding sites in the brain and other tissues. Pharmacological properties have previously included drowsiness, respiratory depression, changes in mood and mental clouding without a resulting loss of consciousness. The term "opioid-like" as used herein refers to compounds that are similar in structure and/or pharmacological profile to known opioid compounds. Examples of opioid and opioid-like compounds, include but are not limited to, endogenous opioid-like peptides that are present particularly in areas of the central nervous system, alfentanil, allylprodine, alphaprodine, anileridine, benzylmorphine, bezitramide, buprenorphine, butorphanol, clonitazene, codeine, cyclazocine, desomorphine, dextromoramide, dextromethorphan, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, morphinan, myrophine, narceine, nicomorphine, norlevorphanol, normethadone, naltrindole, nalorphine, naloxone, nalbuphene, nalmefene, naltrexone, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, and derivatives and analogs thereof.

"Treat" or "treating" as used herein refers to any type of treatment that imparts a benefit to a patient afflicted with a disease, including improvement in the condition of the patient (e.g. in one or more symptoms), delay in the progression of the condition, prevention or delay of the onset of the disease, etc.

As used herein, a "pharmaceutically acceptable" component (such as a salt, carrier, excipient or diluent) means that the compound or composition is suitable for administration to a subject to achieve the treatments described herein, without unduly deleterious side effects in light of the severity of the disease and necessity of the treatment.

"Therapeutically effective amount" as used herein refers to an amount necessary to prevent, delay or reduce the severity of the condition of interest and also includes an amount necessary to enhance normal physiological functioning.

In general, active compounds of the present invention are novel opioid or opioid-like compounds. These novel compounds are useful for preventing or treating diseases or disorders as described herein. Novel compounds according to the present invention comprise a structure according to the formula R-A-X wherein:

R can be H, alkyl, or $(CH_2)_m R_4$, wherein m is from 0 to 6 and $R_4$ can be a ring structure. The ring structure can be aryl including, but not limited to, phenyl, benzyl, naphthyl, and biphenyl, wherein the ring is optionally substituted with one to three substituents selected from the group consisting of halogen, alkyl, $NO_2$, CN, $CF_3$, and lower alkoxy. $R_4$ can be a five-membered heterocyclic ring having one or more heteroatoms selected from the group consisting of O, S, and N, wherein the heterocyclic ring is substituted with a lower alkyl or a substituted phenyl methyl group. $R_4$ can be a pyridine ring wherein the pyridine ring is optionally substituted with halogen, alkyl, $NO_2$, CN, $CF_3$, $OCH_3$, or $NR_1R_2$, where $R_1$ and $R_2$ are each independently H or alkyl, or $R_1$ and $R_2$ is a cyclic ring, wherein the cyclic ring is a 3- to 7-membered alicyclic ring optionally having a double bond in the ring. $R_4$ can be quinoline. $R_4$ can be isoquinoline. $R_4$ can be 4-cyclohexylphenyl. $R_4$ can be a cyclic ring, wherein the cyclic ring is a 3- to 7-membered alicyclic ring optionally having a double bond in the ring;

A can be a structure such as one of the following structures:

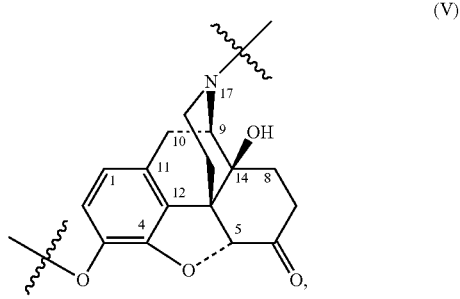

(V)

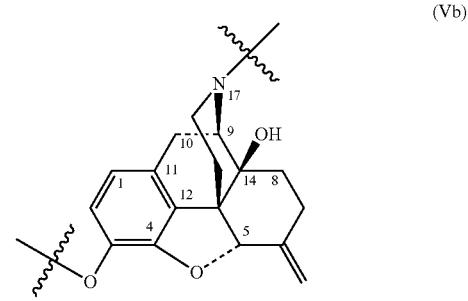

(Vb)

-continued (VI)

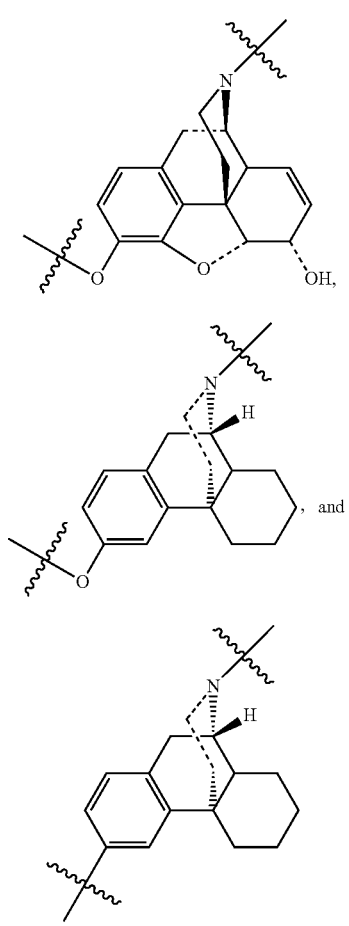

(VII)

(XIX)

IX
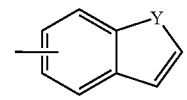

X
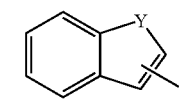

XI
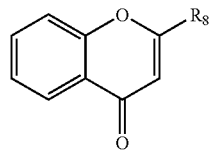

XII
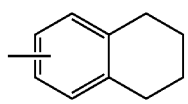

XIII
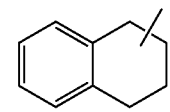

XIV
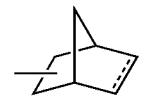

XV
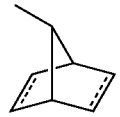

XVI
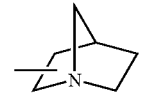

XVII
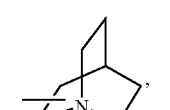, and

XVIII
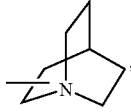

A can be a structure that has an opioid or opioid-like core structure or can be modified to represent an opioid or opioid-like core structure. Such compounds that can provide a core structure include, but are not limited to, alfentanil, allylprodine, alphaprodine, anileridine, benzylmorphine, bezitramide, buprenorphine, butorphanol, clonitazene, codeine, cyclazocine, desomorphine, dextromoramide, dextromethorphan, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, morphinan, myrophine, narceine, nicomorphine, norlevorphanol, normethadone, nalorphine, naloxone, nalbuphene, nalmefene, naltrexone, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, and derivatives and analogs thereof, now known or later identified.

X can be hydrogen, allyl, cinnamoyl, crotonyl, $(CH_2)_nC_6H_5$-4F, $(CH_2)_nC=CR_1R_2$, $(CH_2)_nC\equiv CR_3$, $(CH_2)_nR_5$, and $(CH_2)_mCHR_6R_7$, wherein m is from 0 to 6 and n is from 0 to 6. $R_3$ can be H, alkyl, or the same as $R_4$, wherein $R_4$ is described above and $R_5$ can be alkyl, CN, $COR_8$, or structures selected from the group consisting of the following structures:

wherein Y can be O, S or N. $R_6$ and $R_7$ are each independently the same as $R_4$ as defined above; and $R_5$ is alkyl, the same as $R_4$ as defined above, or the same as $R_5$ when $R_5$ can be the structures described above (IX-XVIII).

When A is of the formula VII and the group $(CH_2)_nC=R_1R_2$ is cinnamyl, it may be appropriate that R is not H, alkyl, allyl or benzyl. For example, a compound of the present invention according to the formula R-A-X can comprise the structure

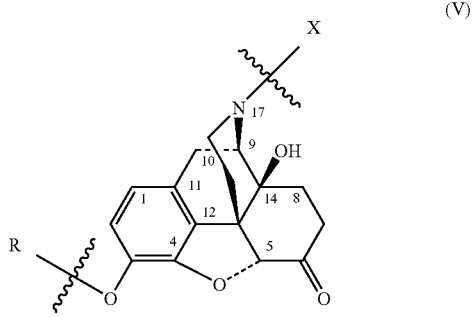

(V)

where R and X are described herein. This example further illustrates the placement of R and X, and thus, substitutents corresponding thereto.

The novel compounds described above do not encompass compounds currently known as of the date of this invention.

Some of the compounds of the present invention described above can possess narcotic and analgesic properties as well as antiviral activities and inhibition of the release and production of superoxide anion TNF-a, and iNOS. However, certain therapeutic effects of the compounds of the present invention can be mediated through mechanisms other than through interaction with opiate receptors. Novel compounds of the present invention described above can be useful for the prevention or treatment of viral infections and diseases, disorders and/or conditions such as septic shock, inflammation, organ damage, neurological disorders, cancer, cardiac disorders, and cardiac disorders, and diseases associated with overproduction of superoxide anion radical, TNF-a, and iNOS, wherein a pharmaceutical composition comprising a therapeutically effective amount of the compound is administered to a subject in need thereof.

Active compounds of the present invention further comprise the use of opioid and opioid-like compounds, now known and later identified, for the prevention and treatment of viral infections and diseases, disorders and/or conditions such as septic shock, organ damage, neurological disorders, neurodegenerative diseases, cancer, and cardiac disorders, and diseases associated with overproduction of superoxide anion radical, TNF-a, and iNOS, wherein a pharmaceutical composition comprising a therapeutically effective amount of the compound is administered to a subject in need thereof. Examples of such opioid and opioid-like compounds include, but are not limited to, alfentanil, allylprodine, alphaprodine, anileridine, benzylmorphine, bezitramide, buprenorphine, butorphanol, clonitazene, codeine, cyclazocine, desomorphine, dextromoramide, dextromethorphan, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, morphinan, myrophine, narceine, nicomorphine, norlevorphanol, normethadone, nalorphine, naloxone, nalbuphene, nalmefene, naltrexone, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, and derivatives and analogs thereof, now known or later identified.

Active compounds of the present invention can be water soluble and can also comprise known water-soluble opioid and opioid-like derivatives.

Compounds of the present invention can possess an asymmetric carbon atom(s) and therefore are capable of existing as enantiomers or diastereoisomers. Thus, compounds of the present invention include enantiomers and diastereoisomers as well as pharmaceutically acceptable salts of the compounds of the present invention.

Active compounds of the present invention can be administered alone or in combination with other therapeutic agents. For example, active compounds of the present invention can be coadministered with compounds now known, or later identified, to be useful for the prevention and or treatment of viral infections and conditions such as septic shock, inflammation, organ damage, neurological disorders, neurodegenerative diseases, cancer, and cardiac disorders, , and diseases associated with overproduction of superoxide anion radical, TNF-a, and iNOS, Exemplary compounds include, but are not limited to, analgesics, anesthetics, antifungals, antibiotics, antiinflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, corticoids (steroids), antidepressants, depressants, diagnostic aids, diuretics, enzymes, expectorants, hormones, hypnotics, minerals, nutritional supplements, parasympathomimetics, potassium supplements, sedatives, sulfonamides, stimulants, sympathornimetics, tranquilizers, urinary antiinfectives, vasoconstrictors, vasodilators, vitamins, xanthine derivatives, and the like.

Opioid compounds and opioid-like compounds can have unwanted side effects in the central nervous system. Therefore, compounds of the present invention in which undesirable side effects are minimal to non-existent are preferred.

A. Synthesis of Compounds

Variations on the following general synthetic methods will be readily apparent to those of ordinary skill in the art and are deemed to be within the scope of the present invention.

A compound having the structural formula R-A-X, wherein A is an opioid skeleton having a structural formula such as shown in formula III, IV, VI or VII, and appropriate substituents or links among W, S, and T which would form a structure of formula III, IV, VI or VII, are prepared according to the reaction scheme shown below in which R and X, unless otherwise indicated, are as defined above.

Scheme 1

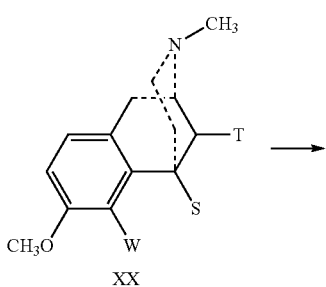

XX

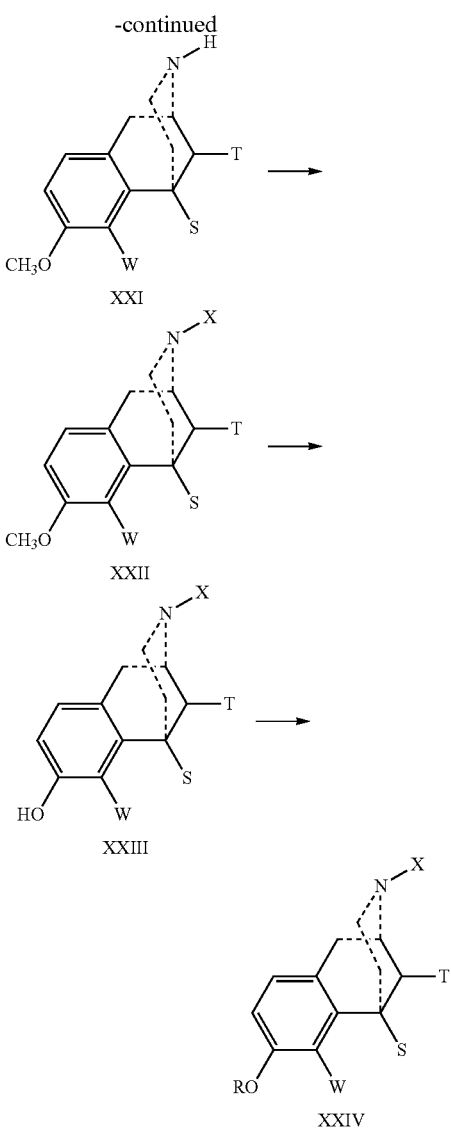

Compounds of formula XXIV are prepared by O-alkylation of a compound of formula XXIII in a base or a catalyst and a polar solvent with a halide, RZ. Z can be halides or a leaving group such as mesyl, tosyl, or triflate. Suitable bases or catalysts include, but are not limited to, potassium carbonate, NaH, KH, sodium or potassium hexamethyldisilazide, and tertiary amines such as trialkylamines, for example, triethylamine, 1,8-diazabicyclo[5.4.0]undec-7-ene(DBU), and 1,5-iazabicyclo[4.3.0]non-5-ene (DBN). Suitable polar solvents include, but are not limited to, ethers, for examples, diethyl ether, glycol dimethyl ether, tetrahydrofuran, dioxane; acetone, dimethylformamide, toluene or acetonitrile. The reaction temperature can be from about room temperature to 150° C.

Compounds of formula XXIII can be prepared by demethylation of a compound of formula XXII with 47% HBr or BBr$_3$ in methylene chloride at a temperature from about −78° C. to 150° C.

Compounds of formula XXII can be prepared by N-alkylation of a compound of formula XXI in a base or a catalyst and a polar solvent with XZ where m≠0. Z is as defined above. The base or the catalyst, the polar solvent and reaction temperature is as defined above for the synthesis of formula XXIV from formula XXIII.

N-arylation of a compound of formula XXI with XZ where m=0 may be performed using a palladium catalyst and Cs$_2$CO$_3$ as the stoichiometric base according to the methods which are described in *Tet. Lett.* 38, 6359-6362 (1997) and *Tet. Lett.* 38, 6363-6366 (1997). X is R$_4$ which represents an aryl group.

Compounds of formula XXI can be prepared by treating of formula XX in 1,2-dichloroethane with 1-chloroethyl chloroformate and potassium carbonate in a temperature from 0° C. to a refluxing temperature in the presence of nitrogen. Formula XX is a commercially available compound.

The present invention contemplates all enantiomers of compounds having formula XXIV. In some embodiments, however, the configuration at C9 is the S-configuration. In other embodiments, the S-configuration is also present at C5 of compounds having formula III.

B. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. In other particular embodiments, pharmaceutically acceptable salts are formed with malic acid. In particular embodiments, pharmaceutically acceptable salts are formed with hydrochloric acid.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

C. Pharmaceutical Formulations

The opioid and opioid-like compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

It will be appreciated that certain compounds of the above formulas can possess an asymmetric carbon atom(s) and are thus capable of existing as enantiomers. Unless otherwise specified, this invention includes such enantiomers, including racemates. The separate enantiomers may be synthesized from chiral starting materials, or the racemates can be resolved by procedures that are well known in the art of chemistry such as chiral chromatography, fractional crystallization of diastereometric salts and the like.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. In one particular embodiment, a pharmaceutical composition comprises less than 80% by weight of active compound. In other particular embodiments, a pharmaceutical composition comprises less than 50% by weight of active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, tablets, dragees, or syrups each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

The present invention may also be formulated into a sustained-release preparation. A sustained-release composition includes, but is not limited to, those in which the active ingredient is bound to an ion exchange resin which is optionally coated with a diffusion barrier to modify the release properties of the resin.

Carriers and/or diluents which may be used include vaseline, lanoline, glycerin, vegetable oils, or fat emulsions, polyethylene glycols, alcohols, transdermal enhancers, natural or hardened oils or waxes, and combinations of two or more thereof.

D. Methods of Use

In addition to the compounds of the formulas described herein, the present invention also provides useful therapeutic methods. For example, the present invention provides a method of treating viral infections and septic shock, inflammation, organ damage, neurological disorders, neurodegenerative diseases, cancer, and cardiac disorders, and diseases associated with overproduction of superoxide anion radical, TNF-a, and iNOS. In some embodiments, viral infections include, but are not limited to, infections by Hepatitis B virus and Hepatitis C virus.

In particular embodiments, organ damage includes, but is not limited to, liver damage, kidney damage, and lung damage. Such damage may arise from causes that include, but are not limited to, alcohol abuse, cirrhosis, hepatitis, and septic shock such as sepsis arising from bacterial infections or environmental toxins such as carbon tetrachloride.

In other particular embodiments, neurological disorders include, but are not limited to seizure disorders such as epilepsy, Tourette Syndrome, stroke, and neurodegenerative diseases including, but not limited to, Parkinson's disease, Alzheimer's disease, cognition deficit disorder, memory loss, amyotrophic lateral sclerosis, and multiple sclerosis.

In particular embodiments, exemplary cancers include, but are not limited to, leukemia, lymphoma, colon cancer, renal cancer, liver cancer, breast cancer, lung cancer, prostate cancer, ovarian cancer, melanoma, small cell lung cancer, testicular cancer, esophageal cancer, stomach cancer, endometrial cancer, central nervous system cancer, and the like. The term "cancer" has its understood meaning in the art, for example, an uncontrolled growth of tissue that has the potential to spread to distant sites of the body (i.e., metastasize). Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive compounds and methods disclosed herein are used to prevent and treat malignant tumors.

In still yet other particular embodiments, cardiac disorders include, but are not limited to, cardiac ischemia, congestive heart failure, and hypertension.

In other particular embodiments, diseases associated with overproduction of superoxide anion radical, TNF-α, or iNOS include, but are not limited to, Alzheimer's disease, Parkinson's disease, aging, cancer, myocardial infarction, atherosclerosis, autoimmune disease, radiation injury, emphysema, sunburn, joint disease, and oxidative stress. Suitable subjects to be treated according to the present invention include both avian and mammalian subjects, preferably mammalian. Mammals according to the present invention include but are not limited to canine, felines, bovines, caprines, equines, ovines, porcines, rodents (e.g. rats and mice), lagomorphs, primates, and the like, and encompass mammals in utero. Humans are preferred.

Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Any mammalian subject in need of being treated according to the present invention is suitable. Human subjects are preferred. Human subjects of both genders and at any stage of development (i.e., neonate, infant, juvenile, adolescent, adult) can be treated according to the present invention.

As noted above, the present invention provides pharmaceutical formulations comprising the compounds of formulae described herein, or pharmaceutically acceptable salts thereof, in pharmaceutically acceptable carriers for any suitable route of administration, including but not limited to, oral, rectal, topical, buccal, parenteral, intramuscular, intradermal, intravenous, and transdermal administration.

According to the present invention, methods of this invention comprise administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the compounds of the present invention can be administered to the subject in an amount ranging from a lower limit from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, or 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% by weight of the composition. In some embodiments, the compounds comprise from about 0.05 to about 95% by weight of the composition. In other embodiments, the compounds comprise from about 0.05 to about 60% by weight of the composition. In still other embodiments, the compounds comprise from about 0.05 to about 10% by weight of the composition.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, compounds of the present invention may be administered at a daily dosage of from about 0.1 mg to about 20 mg per kg of animal body weight, which can be given in divided doses q.d. to q.i.d. or in a sustained release form. For humans, the total daily dose may be in the range of from about 5 mg to about 1,400 mg, and in other particular embodiments, the total daily dose is in the range of from about 10 mg to about 100 mg. In still other embodiments, the unit dosage forms suitable for oral administration may comprise about 2 mg to about 1,400 mg of the compound optionally admixed with a solid or liquid pharmaceutical carrier or diluent. The compounds of the present invention can be administered in any amount appropriate to administer to the subject for treatment of the condition desired to be treated as determined by one of ordinary skill in the art by reference to the pertinent texts and literature and/or by using routine experimentation. (See, for example, Remington, *The Science And Practice of Pharmacy* (9th Ed. 1995). However, in general, satisfactory results are obtained when the compounds of the invention are administered at a daily dosage of from about 0.1 mg to about 20 mg per kg of animal body weight, preferably given in divided doses 1 to 4 times a day or in sustained release form.

The present invention is explained in greater detail in the following non-limiting examples.

EXAMPLE 1

(+)-3-methoxy-17-allylmorphinan Hydrobromide

A solution of 11.0 g (3.41 mmol) of (+)-3-methoxy-morphinan hydrochloride in tetrahydrofuran (THF) (20 mL) was added to triethylamine 1.3 mL (10.26 mmol). After stirring for 30 minutes, allyl bromide 0.52 mL (6.82 mmol) was added. The resulting mixture was stirred for 8 hours at room temperature (20-25° C.). Then the mixture was evaporated and partitioned with $CH_2Cl_2$ (40 mL) and water (20 mL). The $CH_2Cl_2$ layer was separated, dried over $MgSO_4$, and evaporated to afford crude product (700 mg). The yield was 69%. The crude product was dissolved in $CH_2Cl_2$ (15 mL), and then 48% hydrobromic acid (0.5 mL) was slowly added with stirring over 10 min. The solution was evaporated and pump dried. The crude was recrystallized from ethyl acetate to afford HBr (560 mg) as light yellow powder. Total yield was 63%; mp 190-192° C.; mass spectroscopy recorded on a Finnigan MAT95S mass spectrometer: MS (EI, 70 eV) m/z 297 ($M^+$), 270; HRMS calculated for $C_{20}H_{27}NO^+$: 297.2093, found: 297.2087.

EXAMPLE 2

(+)-3-methoxy-17-benzylmorphinan Hydrobromide

A solution of 1.0 g (3.41 mmol) of (+)-3-methoxy-morphinan hydrochloride in THF (20 mL) was added to triethylamine 0.88 mL (6.84 mmol). After stirring for 30 min., benzyl bromide 0.40 mL (3.41 mmol) was added. The resulting mixture was stirred for 6 hours at room temperature. Then the mixture was evaporated and partitioned with $CH_2Cl_2$ (40 mL) and water (20 mL). The $CH_2Cl_2$ layer was separated, dried over MgSO$_4$, and evaporated to afford crude product. The crude product was chromatographed (CH$_2$Cl$_2$:MeOH=15:1) to get yellow liquid. The liquid was dissolved in CH$_2$Cl$_2$ (15 mL), and then 48% hydrobromic acid (0.5 mL) was slowly added with stirring over 10 min. The solution was evaporated and dried with pump. The crude was recrystallized from CH$_2$Cl$_2$ and ethyl acetate to afford 3 HBr (560 mg) as light yellow crystals. Total yield was 38%; mp 185-186° C.; MS (EI 70 eV) m/z 347 (M$^+$), 226; HRMS calculated for C$_{24}$H$_{29}$NO$^+$: 347,2249, found: 347.2227.

EXAMPLE 3

(+)-3-methoxy-17-(4-fluorobenzyl)morphinan Hydrobromide

A solution of 1.0 g (3.41 mmol) of (+)-3-methoxy-morphinan hydrochloride in THF (20 mL) was added to triethylamine 0.88 mL (6.84 mmol). After stirring for 30 min., 4-fluorobenzyl bromide 0.42 mL (3.41 mmol) was added. The resulting mixture was stirred for 20 hours at room temperature. Then the mixture was evaporated and partitioned with CH$_2$Cl$_2$ (40 mL) and water (20 mL). The CH$_2$Cl$_2$ layer was separated, dried over MgSO$_4$, and evaporated to afford crude product. The crude product was chromatographed (CH$_2$Cl$_2$:MeOH=15:1) to get colorless liquid. The liquid was dissolved in CH$_2$Cl$_2$ (15 mL), and then 48% hydrobromic acid (0.5 mL) was slowly added with stirring over 10 min. The solution was evaporated and pump dried. The crude was recrystallized from ethyl acetate to afford HBr (980 mg) as colourless crystals. Total yield was 64%; mp 226-228° C.; MS (EI, 70 eV) m/z 365(M$^+$); HRMS calculated for C$_{24}$H$_{28}$FNO$^+$: 365.2155, found: 365.2146.

EXAMPLE 4

(+)-3-Methoxy-17-(trans-cinnamylbenzyl)morphinan Hydrobromide

A solution of 1.0 g (3.41 mmol) of (+)-3-methoxy-morphinan hydrochloride in THF (20 mL ) was added to triethylamine 0.88 mL (6.84 mmol). After stirring for 30 min., cinnamyl bromide 0.64 mL (3.41 mmol) was added. The resulting mixture was stirred for 19 hours at room temperature. Then the mixture was evaporated and partitioned with CH$_2$Cl$_2$ (40 mL) and water (20 mL). The CH$_2$Cl$_2$ layer was separated, dried over MgSO$_4$, and evaporated to afford crude product. The crude product was chromatographed (CH$_2$—Cl$_2$:MeOH=15:1) to get yellow liquid. The crude liquid was dissolved in CH$_2$Cl$_2$ (15 mL), and then 48% hydrobromic acid (0.5 mL) was slowly added with stirring over 10 min. The solution was evaporated and pump dried to afford compound HBr as yellow foam liquid. MS (EI, 70 eV) m/z 373 (M$^+$); HRMS calculated for C$_{26}$H$_3$,NO$^+$: 373.2406, found: 373.2388.

EXAMPLE 5

(+)-3-methoxy-17-(3-pyridylmethy)morphinan Hydrobromide

Similarly to the preparation of Example 4, the title compound was prepared from the reaction of (+)-3-methoxy-morphinan hydrochloride (1 g, 3.4 mmol) in THF (20 ml), triethylamine (1.43 ml, 10.3 mmol), and 3-(bromomethyl)pyridine hydrobromide (0.95 g, 3.75 mmol) gave a solid which was treated with 45% HBr to afford 1 g of a tan solid (68% yield); ms (ESI+): m/z 349 (M+1).

EXAMPLE 6

(+)-3-methoxy-17-(2-thienylmethyl)morphinan Hydrobromide

Similarly to the preparation of the above examples, the title compound is prepared from (+)-3-methoxy-morphinan hydrochloride in THF (20 ml), triethylamine 0.88 mL (6.84 mmol), 2-thienylmethanol mesylate (3.41 mmol).

2-thienylmethanol mesylate is prepared by treating a solution of 2-thienylmethanol (5.57 g; 50 mmol) in methylene chloride (100 ml) and triethylamine (15.05 g, 150 mmol) at 0° C. with methanesulfonyl chloride (11.45 g, 100 mmol) dropwise and at RT 1 hr after the addition. The reaction mixture is poured into ice-water and the organic layer is separated, dried (MgSO4), and evaporated.

EXAMPLE 7

(+)-3-methoxy-17-acetyl-morphinan

Acetic anhydride (3.14 g, 30.76 mmol) was added to a solution of (+)-3-methoxy-morphinan hydrochloride (1.5 g, 5.1 mmol) in THF (30 ml) and triethylamine (8.7 g, 85.98 mmol) in the presence of nitrogen. The resulting solution was heated at 60° C. for 15 hr. The reaction mixture was cooled to room temperature and evaporated under vacuum. The residue was dissolved in methylene chloride (50 ml), washed with water (40 ml×2) and dried (MgSO4). Evaporation of the dried solution gave a tan viscous oil (1.25 g, 81% yield); ms (ESI+): m/z 300(M+1).

EXAMPLE 8

(+)-3-methoxy-17-trans-crotonyl-morphinan

Thionyl chloride (18.3 ml) was added to a solution of trans-crotonic acid (20 g) in toluene (5 ml) and stirred. The resulting solution was stirred at a temperature below 10° C. for 4 hr and thereafter thionyl chloride was distilled off. The residue was evaporated under vacuum to give a brown residue of crotonyl chloride and used directly. A solution of (+)-3-methoxy-morphinan hydrochloride (0.5 g, 1.5 mmol) in toluene (15 ml) and triethylamine (0.5 ml, 3.5 mmol) was stirred for 5 min and tlc (Ethyl acetate:hexane=1:1) indicated that the reaction was complete. The reaction mixture was washed with water (200 ml) and the organic layer was evaporated under vacuum. This gave a viscous oil. The oil was further purified by a silica gel column eluting with ethyl acetate:hexane (1:1) to give a light tan oil; ms (ESI+): m/z 362 (M+1).

EXAMPLE 9

(+)-3-methoxy-17-(indole5-carbonyl)-morphinan

Oxalyl chloride (15 ul, 0.14 mmol) at RT was added to a solution of indole-5-carboxylic acid (0.02 g, 0.12 mmol) in THF (1 ml). After stirring at RT for 10 h, the mixture was added THF (1 ml) followed by (+)-3-methoxy-morphinan hydrochloride (0.04 g, 0.12 mmol), then triethylamine (0.1 ml, 0.7 mmol) was added and stirred for 18 h. The reaction mixture was filtered and washed with ethyl acetate. The filtrate was washed with saturated Na$_2$CO$_3$ (5 ml), dried (Na$_2$SO$_4$), filtered and concentrated at reduced pressure to give a crude pale brown oil. The crude product was purified by column chromatographed eluting with (MeOH: CH$_2$Cl$_2$=1:10) to give a pale yellow oil (0.013 g, 28% yield).

EXAMPLE 10

(+)-3-methoxy-17-(indole-5-methyl)-morphinan

Lithium aluminum hydride (1 M in THF; 0.1 ml, 0.1 mmol) was added to a solution of the amide, Example 9, (0.013 g, 0.033 mmol) in THF (1 ml) at 0° C. The mixture was heated at reflux for 5 h, then was cooled to 0° C., and treated with 3% aq NaOH (1.5 ml). The mixture was filtered through a pad of Celite and the filtrate was dried over anhyd. Na$_2$SO$_4$, and evaporated the dried solution to give a pale yellow oil (0.010 g); MS (EI): m/z 402 (M)

EXAMPLE 11

(+)-3-methyl-17-methyl-morphinan (+)-1-p-methylbenzyl-2-methyl-1,2,3,4,5,6,7,8-octahydroisoquinoline (26.5 g) was added to 85% phosphoric acid (130 ml) and the mixture was heated to 130-140° C. for 72 h. After the reaction was complete, the reaction mixture was poured into ice-water and the solution was made strongly alkaline by the addition of conc. ammonia solution (about 300 ml) and diluted with water (500 ml). The solution was then extracted with ether (500 ml×2). The ether layers were combined and washed with water (200 ml), and dried (K$_2$CO$_3$), filtered and evaporated to yield an oil. The oil was immediately vacuum-distilled to produce a faint yellow oil (10 g; bp 130-136° C./0.3 mm Hg) which was crystallized on standing. Recrystallization from acetone (~10 ml) provided white prisms ((7.3 g) of (+)-3-methyl-17-methyl-morphinan; MS (ESI+): m/z 256 (M+1). This procedure is similar to the procedure in U.S. Pat. No. 3,786,054, incorporated by reference herein in its entirety.

EXAMPLE 12

(+)-3-methoxy-17-[2-(1-azabicyclo[2.2.1]heptanyl)]morphinan Hydrobromide

A solution of 1.0 g (3.41 mmol) of (+)-3-methoxy-morphinan hydrochloride in anhyd. hexamethylphosphrous triamide (20 mL) and triethylamine 0.88 mL (6.84 mmol) is stirred at room temperature for 30 min. The resulting mixture is treated with 2-bromo-1-azabicyclo[2.2.1]heptane (0.60 g, 3.41 mmol) and heated under reflux for 48 hr. Then the mixture is cooled, diluted with ethyl acetate (100 ml), washed with water (20 ml×3) and saturated brine (10 ml), dried (MgSO$_4$) and evaporated to afford an oil. The oil product is purified through a silica gel column (CH$_2$Cl$_2$:MeOH=15:1) to give a free base of the title compound. To a solution of the purified product in CH$_2$Cl$_2$ is added slowly 48% hydrobromic acid (0.5 mL) with stirring over 10 min. The solution is evaporated and dried under high vacuum to afford the HBr salt of the title compound.

EXAMPLE 13

(+)-3-methoxy-17-(4-nitrophenyl)morphinan

Pd(OAc)$_2$ (1.34 mg, 0.006 mmol) and 10% solution of P(t-Bu)$_3$ in hexane (0.015 ml, 0.0048 mmol) were added to the suspension of NaO-t-Bu (86.4 g, 0.9 mmol), (+)-3-methoxy-morphinan (0.1645 g, 0.5 mmol) and 4-(nitro)-bromobenzene (0.1212 g, 0.6 mmol) in toluene (~12 mL) in the presence of nitrogen. The resulting mixture was heated at 80° C. for 6 h. The reaction mixture was allowed to cool to room temperature, diluted with methylene chloride (50 mL), and washed with water. Concentration of the organic layer and flash chromatography on silica gel was carried out eluting with hexane first and then with a 5% to 20% ethyl acetate solution in hexane to provide a yellow liquid, 56.4 mg (30% yield); ms (EI): m/z 378 (M).

EXAMPLE 14

(+)-3-methoxy-17-(quinuclidinyl-3-carbonyl)-morphinan

Similar to the preparation of indole-5-carboxyl chloride, 1-azabicyclo[2.2.2.]octane-3-carboxylic acid or quinuclidinyl-3-carboxylic acid or compounds described in Orlek, B. S. et al, *J. Med. Chem.* 34(9), 2726-2735 (1991) are converted to quinuclidinyl-3-carboxyl chloride. The chloride is allowed to react with (+)-3-methoxy-morphinan hydrochloride as described in the preparation of Example 9 to provide the title compound as shown below.

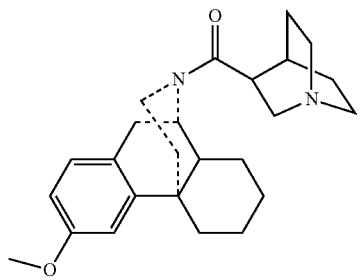

EXAMPLE 15

(+)-3-methoxy-17-(quinuclidinyl-3-methyl)-morphinan

The compound is synthesized by treating the amide from Example 13 with lithium aluminum hydride in a manner similar to the preparation of Example 10. The resulting compound is shown below.

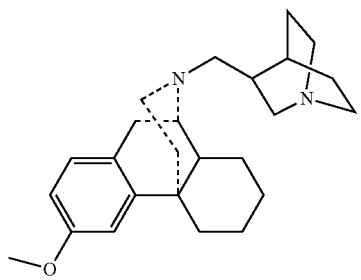

EXAMPLE 16

(+)-3-methoxy-17-(phenyl)morphinan

Similar to the preparation of the compound of Example 13, the title compound is made from the reaction of Pd(OAc)$_2$ (1.34 mg, 0.006 mmol), 10% solution of P(t-Bu)$_3$ in hexane (0.015 ml, 0.0048 mmol), and NaO-t-Bu (86.4 g, 0.9 mmol) in the presence of argon and then a solution of (+)-3-methoxymorphinan (0.1645 g, 0.5 mmol) and bromobenzene (0.094 g, 0.6 mmol) in toluene (~12 mL).

EXAMPLE 17

Pharmacological Testing

The pharmacological activity of the compounds of the present invention may be measured in the tests set out below.

In Vivo Experiments

Wistar-Kyoto (WKY) rats were anesthetized by intraperitoneal injection of urethane (1.2 g/kg). The trachea was cannulated to facilitate respiration and environmental temperature was maintained at 24° C. with an air-conditioning system. The right carotid artery was cannulated and connected to a pressure transducer (P231D, Statham, Oxford, Calif.) for the measurement of phasic blood pressure and mean arterial blood pressure (MAP) as well as heart rate (HR), which were displayed on a Gould model TA5000 polygraph recorder (Gould Inc., Valley View, Ohio). The left jugular vein was cannulated for the administration of drugs. Upon completion of the surgical procedure, cardiovascular parameters were allowed to stabilize for 30 min. After recording baseline hemodynamic parameters, animals were given norepinephrine [NE, 1 µg/kg intravenously (i.v.)], and 10 min later animals received vehicle (saline) or *Escherichia coli* lipopolysaccharide (LPS), 5-10 mg/kg, i.v. and were monitored for 360 min. The pressor responses to NE were reassessed every hour after vehicle or LPS injection. Prior to (i.e., at time 0) and every hour after vehicle or LPS, 0.5 mL of blood was taken to measure the changes in cytokine tumor necrosis factor-α (TNF-α), interleukin-10β (IL-10), and nitrate (an indicator of NO) (Yen, M. H. et al., *Shock* 14, 60-67, 2000). Any blood withdrawn was immediately replaced by the injection of an equal volume of saline (i.v.) in order to maintain the blood volume. The drug was administered i.v. 30 min. prior to and 30 min. after the injection of LPS. All hemodynamic and biochemical parameters were recorded for 6 hours in all animal groups.

Measurement of TNF-α and IL-10 in Plasma Levels

Blood samples (0.3 mL) for the measurement of TNF-α level in the plasma were obtained at 0, 60, 120, 180, and 360 min. after the injection of saline or LPS. At 60 and 360 min. after the injection of saline or LPS, the volume of blood sample taken from the animals was 0.5 mL instead of 0.3 mL for performing the measurement of IL-10 in addition to TNF-α. These samples were collected from a catheter placed in the carotid artery and were centrifuged at 7200 g for 3 min. to obtain the plasma for measuring the levels of TNF-α, IL-10, and nitrate (as described below). The plasma samples (100 µL) were diluted 1:2, and TNF-α was measured in duplicate with an enzyme-linked immunoadsorbent assay (ELISA) kit (Genzyme Co., Cambridge, Mass.), and the amounts of IL-10 in the plasma (100 µL) were measured by ELISA kit (Endogen Inc., Boston, Mass.), as described previously (Yen, M. H. et al.: *Biochem. Biophys. Res. Commun.* 228:459-466 (1996)).

Determination of Plasma Nitrate

Fifty microliters of plasma previously kept in −20° C. freezer was thawed and de-proteinized by incubating with 95% ethanol (4° C.) for 30 min. The samples were subsequently centrifuged for an additional 5 min. at 14,000 g. It is noted that the nitrate concentration in plasma depicted in the study is actually the total nitrite and nitrate concentration in plasma. In this method, nitrate is reduced to NO via nitrite. The amounts of nitrate in the plasma (2 p.L) were measured by adding a reducing agent (0-8% VCl$_3$ in 1N HCl) to the purge vessel to convert nitrate to NO, which was stripped from the plasma by using a helium gas purge. The NO was then drawn into the Sievers Nitric Oxide Analyzer (Sievers 280 NOA, Sievers Inc., Boulder, Colo.). Nitrate concentrations were calculated by comparison with standard solutions of sodium nitrate (Sigma Chemical Co., St. Louis, Mo.).

Measurement of Serum Glutamic Oxaloacetic Transaminase (SGOP) and Serum Glutamic Pyrate Transaminase (SGTP)

10 µl of serum was taken out at 0 and 6 hr intervals and were added to slides of GOP and GTP and then placed in DRI-CHEM 3000(Colorige Tric Analyzer; FUJIFILM; Tokyo, Japan Determination of Blood Urea Nitrogen (BUN) and Plasma Creatinine BUN and Creatinine levels were measured at 0 and 6 hr after injection of saline or LPS by "DRI-Chemical slide" (Fujifilm Co., dropping 10 µL plasma onto the slide with micropipette).

Survival Studies

Survival studies were performed in ICR mice (28-35 g), whose stock originated from the Institute of Cancer Research of National Institute of Health in U.S.A. They were purchased from the National Animal Center (Taipei, R.O.C., Taiwan). LPS [60 mg/kg intraperitoneally (i.p.)] was injected in the presence of vehicle or drugs and survival was monitored every 6 hours until 36 hours. Different groups of animals received vehicle (saline) together with LPS (n=20) or LPS plus compounds (2.5 mg/kg at time 0 and 6 hours after LPS, n=20).

Histological Studies

Lungs and livers were obtained from surviving mice in each group after the survival study and these tissues were fixed in Carson-Millonig's solution for histopathological examination as described previously in Chen, A. et al. *Lab. Invest.* 67, 175-185 (1992). The fixed lung and liver tissues were dehydrated in graded ethanol and embedded in paraffin. Three-micron sections were stained with the hematoxylin and eosin reagent for light microscopy. In preliminary experiments, a striking pathological feature of the mice receiving LPS was a prominent infiltration of neutrophils in the organs studied. This histological alteration was quantitatively analyzed as an index on the severity of tissue injury. This index was a neutrophil infiltration index which was determined by counting the numbers of neutrophils in 10 randomly selected high power fields. The index was expressed as the mean of these 10 numbers±standard error of the mean (SEM)/high power field.

Statistical Analysis

All values in the figures and text are expressed as mean. SEM of n observations, where n represents the number of animals studied. Statistical evaluation was performed by using analysis of variance (ANOVA) followed by a multiple comparison test (Scheffe's test), the IL-10 level and the neutrophil infiltration index which were analyzed by unpaired Student's t test. The chi-square test was used for determining the significant differences in the survival rate between control and drug-treated groups. A P value of less than 0.05 was considered to be statistically significant.

EXAMPLE 18

Serum Glutamic Oxaloacetic Transaminase (SGOT)

At 0 hr, the average of SGOT in the control group was 60±6 U/L. When animals were given LPS, the plasma concentration of the SGOT increased as a function of time. XXV (R=methyl, A=V, X=cyclopropylmethyl) (shown below) exhibited significant decrease (p☐0.050☐ of SGOT 6 hours after LPS administration in both pretreatment (30 min before LPS; 5, 10 mg/kg) and post-treatment (30 min after LPS; 10 mg/kg) groups.

EXAMPLE 19

Serum Glutamic Pyrate Transaminase (SGPT)

At 0 hr, the average of SGTP in the control group was 30±4 U/L. When animals were given LPS, the plasma concentration of the SGTP increased as a function of time. Similarly, XXV exhibited a significant decrease (p☐0.05) of SGTP 6 hours after LPS administration in both pretreatment (30 min before LPS; 5, 10 mg/kg) and post-treatment (30 min after LPS; 10 mg/kg) groups.

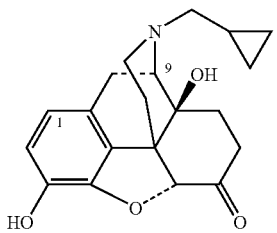

XXV

EXAMPLE 20

Results

Compounds, XXV and XXVI (shown below), were tested according to the foregoing protocols. The results are summarized in Table I as shown below. In the following tables, XXV or XXVI (5 mg/Kg, iv) was injected 30 min before LPS treatment (10 mg/Kg, iv) unless otherwise indicated. In all experiments, at least six rats were tested. All measurements were performed 6 h after LPS injection unless otherwise indicated. The inhibitory effects of the compounds tested were described as a percentage of protection or inhibition with respect to the change in LPS-treated animals as compared to the control animals.

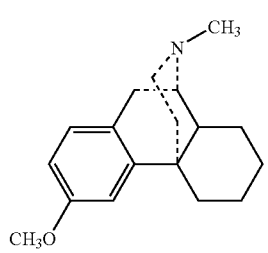

XXVI

TABLE 1

Cardiovascular Effects

| Parameters | Compound # | Control | LPS | LPS + Compound | % Protection |
|---|---|---|---|---|---|
| MAP (mmHg) | XXV | 105 | 60 | 80 | 33 |
|  | XXVI | 105 | 58 | 105 | 100 |
| Heart Rate (beats/min) | XXV | 430 | 355 | 410 | >90% |
|  | XXVI | 384 | 440 | 420 | 36% |

TABLE 2

Free Radicals and TNF-α

| Parameters | Compound # | Control | LPS | LPS + Compound | % Inhibition |
|---|---|---|---|---|---|
| Superoxide (relative units) | XV (10 mg)[2] | 8500 | 31572 | 11866 | 85 |
|  | XV (10 mg)[3] | 8500 | 31572 | 15720 | 69 |
|  | XXVI | 4500 | 15800 | 8200 | 68 |
| Nitrate (uM) | XXVI | 30 | 180 | 75 | 75 |
| TNF-α (ng/ml)[1] | XXV | 60 | 300 | 180 | 50 |
|  | XXVI | 40 | 1800 | 510 | 74 |

[1]The measurement was taken at 2 h.
[2]Pretreatment with 10 mg/Kg.
[3]Post-treatment with 10 mg/Kg.

TABLE 3

Liver Functions

| Parameters | Compound # | Control | LPS | LPS + Compound | % Inhibition |
|---|---|---|---|---|---|
| SGOT (U/L) | XXV | 105 | 328 | 192 | 60 |
|  | XXV (10 mg/Kg)[1] | 105 | 328 | 192 | 94 |
|  | XXV (10 mg/Kg)[2] | 105 | 328 | 192 | 76 |
|  | XXVI | 118 | 286 | 158 | 53 |
| SGPT (U/L) | XXV | 51.4 | 98 | 61.6 | 78 |
|  | XXV (10 mg/Kg)[1] | 51.4 | 98 | 53.8 | 94 |
|  | XXV (10 mg/Kg)[2] | 51.4 | 98 | 559.6 | 82 |
|  | XXVI | 38 | 42 | 36 | 100[3] |

[1]Pretreatment with 10 mg/Kg.
[2]Post-treatment with 10 mg/Kg.
[3]Not statistically significant.

TABLE 4

Kidney Function

| Parameters | Compound # | Control | LPS | LPS + Compound | % of Inhibition |
|---|---|---|---|---|---|
| Blood urine nitrogen (mg/dL) | XXVI | 30 | 58 | 45 | 47 |
| Creatinine mg/dL | XXVI | 0.28 | 0.58 | 0.40 | 60 |

TABLE 5

| | | Mortality | | | |
|---|---|---|---|---|---|
| Parameters | Compound # | Control | LPS | LPS + Compound | % of Protection |
| % of Survival at 14 h | XXVI | 100 | 38 | 100 | 100 |
| % of Survival at 18 h | XXVI | 100 | 0 | 40 | 40 |

The foregoing is illustrative of the present invention, and is not to be construed as limiting thereof. The invention is defined by the following claims, with equivalents of the claims to be included therein.

What is claimed is:

1. A method of treating Crohn's Disease, comprising administering to a subject in need thereof, a pharmaceutical composition comprising a therapeutically effective amount of a compound of naltrexone.

2. A method for treating Crohn's Disease as in claim 1 comprising administering to a subject in need thereof, a pharmaceutical composition comprising a daily dose of from 2 mg to 100 mg of naltrexone.

3. A method of treating Crohn's Disease, comprising administering to a subject in need thereof, a pharmaceutical composition comprising a therapeutically effective amount of a compound of nalmefene.

4. A method for treating Crohn's Disease as in claim 3 comprising administering to a subject in need thereof, a pharmaceutical composition comprising a daily dose of from 2 mg to 100 mg of nalmefene.

5. A method for treating liver damage caused by hepatitis comprising administering to a subject in need thereof, a pharmaceutical composition comprising a therapeutically effective amount of naltrexone and measuring the decrease of at least one of the enzymes SGOT and SGPT in the subject being treated.

6. A method for treating liver damage as in claim 5, comprising administering to a subject in need thereof, a pharmaceutical composition comprising a daily dose of from 2 mg to 100 mg of naltrexone and measuring the decrease of at least one of the enzymes SGOT and SGPT in the subject being treated.

7. A method for treating liver damage caused by hepatitis comprising administering to a subject in need thereof, a pharmaceutical composition comprising a therapeutically effective amount of nalmefene and measuring the decrease of at least one of the enzymes SGOT and SGPT in the subject being treated.

8. A method for treating liver damage as in claim 7, comprising administering to a subject in need thereof, a pharmaceutical composition comprising a daily dose of from 2 mg to 100 mg of nalmefene and measuring the decrease of at least one of the enzymes SGOT and SGPT in the subject being treated.

9. The method according to claim 1, 3, 5, or 7, wherein the pharmaceutical composition is administered orally.

10. The method according to claim 1, 3, 5, or 7, wherein the pharmaceutical composition is administered parentally.

* * * * *